US012616808B2

(12) United States Patent     (10) Patent No.:   US 12,616,808 B2

Peter et al.          (45) Date of Patent:       May 5, 2026

(54) PROCESS AND DEVICE FOR DETECTION OF A LEAK IN A VENTILATION CIRCUIT

(71) Applicant: Drägerwerk AG & Co. KGaA, Lübeck (DE)

(72) Inventors: Gerd Peter, Lübeck (DE); Martin Kroh, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1142 days.

(21) Appl. No.: 17/242,873

(22) Filed: Apr. 28, 2021

(65) Prior Publication Data

US 2021/0338950 A1     Nov. 4, 2021

(30) Foreign Application Priority Data

Apr. 29, 2020    (DE) ..................... 10 2020 002 570.6

(51) Int. Cl.
| | |
|---|---|
| *A61M 16/00* | (2006.01) |
| *A61M 16/08* | (2006.01) |
| *A61M 16/10* | (2006.01) |

(52) U.S. Cl.
CPC ...... *A61M 16/0003* (2014.02); *A61M 16/085* (2014.02); *A61M 16/10* (2013.01);
(Continued)

(58) Field of Classification Search
CPC .... A61M 16/10; A61M 16/18; A61M 16/104; A61M 2016/1025; A61M 2016/103;
(Continued)

(56) References Cited

U.S. PATENT DOCUMENTS

| | | | |
|---|---|---|---|
| 8,033,280 B2 | 10/2011 | Heinonen | |
| 8,221,530 B2 | 7/2012 | Peter et al. | |

(Continued)

FOREIGN PATENT DOCUMENTS

| | | |
|---|---|---|
| CN | 101547716 A | 9/2009 |
| CN | 102164540 A | 8/2011 |

(Continued)

OTHER PUBLICATIONS

Machine translation of DE-102017011625-A1 accessed Apr. 7, 2024 (Year: 2024).*

(Continued)

*Primary Examiner* — Kendra D Carter
*Assistant Examiner* — Maap Ellabib
(74) *Attorney, Agent, or Firm* — McGlew and Tuttle, P.C.

(57) ABSTRACT

A process for monitoring a measuring system (110) for mechanical ventilation of a patient (20) is carried out while a fluid connection (40) is established between the patient (20) and a medical device (100). A gas sample is suctioned from the fluid connection (40) and is sent through a gas sensor fluid-guiding unit (52) to a gas sensor array (50). A time curve of the CO2 concentration and O2 concentration in the suctioned gas sample are determined. A concentration change curve of the change over time of the CO2 concentration and the O2 concentration are calculated. A search is made for a time period in which the two concentration change curves continuously have the same sign. Upon detecting such a time period it is checked whether a predefined first leak criterion is met. When this is the case, an indication of a leak (L) is detected.

10 Claims, 11 Drawing Sheets

(52) U.S. Cl.
CPC .............. *A61M 2016/1025* (2013.01); *A61M 2016/103* (2013.01); *A61M 2205/15* (2013.01)

(58) Field of Classification Search
CPC ........ A61M 2016/024; A61M 2016/01; A61M 2205/15; A61M 2202/0208; A61M 2230/432; A61M 2230/435; A61M 2230/437; A61M 2230/43
See application file for complete search history.

(56) References Cited

U.S. PATENT DOCUMENTS

| | | | |
|---|---|---|---|
| 8,291,903 B2 | 10/2012 | Maxeiner et al. | |
| 8,424,529 B2 | 4/2013 | Efrati et al. | |
| 8,752,544 B2 | 6/2014 | Bottom | |
| 2007/0107728 A1 | 5/2007 | Ricciardelli et al. | |
| 2008/0202526 A1 | 8/2008 | Heinonen | |
| 2010/0263671 A1 | 10/2010 | Walker et al. | |
| 2011/0196251 A1 | 8/2011 | Jourdain et al. | |
| 2012/0240928 A1 | 9/2012 | Bottom | |
| 2013/0253336 A1 | 9/2013 | Haveri | |
| 2013/0317765 A1* | 11/2013 | Rao | A61M 16/0069 702/51 |
| 2017/0182267 A1* | 6/2017 | Cameron | A61M 11/042 |
| 2019/0099542 A1 | 4/2019 | Kuzelka | |
| 2019/0224434 A1* | 7/2019 | Silver | A61M 16/0488 |
| 2020/0353197 A1 | 11/2020 | Peter et al. | |

FOREIGN PATENT DOCUMENTS

| | | | | | |
|---|---|---|---|---|---|
| CN | 102302817 | A | 1/2012 | | |
| CN | 105963835 | A | 9/2016 | | |
| DE | 102007046533 | B3 | 7/2008 | | |
| DE | 102008047980 | A1 | 4/2010 | | |
| DE | 102009024040 | A1 | 12/2010 | | |
| DE | 102010050678 | B3 | 4/2012 | | |
| DE | 102017011625 | A1 * | 12/2017 | ......... | A61M 16/085 |
| EP | 1961439 | A1 | 8/2008 | | |
| EP | 1974763 | A1 | 10/2008 | | |
| EP | 2914321 | B1 | 9/2015 | | |
| WO | 2004076944 | A2 | 9/2004 | | |
| WO | 2009123981 | A1 | 10/2009 | | |
| WO | 2012012835 | A2 | 2/2012 | | |
| WO | 2012085753 | A1 | 6/2012 | | |
| WO | 2014/068000 | A1 | 5/2014 | | |
| WO | 2018/112588 | A1 | 6/2018 | | |
| WO | 2019115571 | A1 | 6/2019 | | |

OTHER PUBLICATIONS

Vishnoi R et al., "Adaptive Control of Closed-Circuit Anesthesia", IEEE Transactions on Biomedical Engineering, IEEE Service Center, Piscataway, NJ, USA, Bd. 38, Nr. 1, Jan. 1, 1991 (Jan. 1, 1991), pp. 39-46, XP000225246, ISSN: 0018-9294, DOI: 10.1109/10.68207.

* cited by examiner

1

PROCESS AND DEVICE FOR DETECTION OF A LEAK IN A VENTILATION CIRCUIT

CROSS REFERENCE TO RELATED APPLICATIONS

This application claims the benefit of priority under 35 U.S.C. § 119 of German Application 10 2020 002 570.6, filed Apr. 29, 2020, the entire contents of which are incorporated herein by reference.

TECHNICAL FIELD

The present invention pertains to a process and to a device for automatically detecting a leak during a mechanical ventilation of a patient, wherein this leak may have an effect on the measurement of gas concentrations, which occur in a fluid connection between a medical device and the patient.

TECHNICAL BACKGROUND

A fluid connection is established between a ventilator and the patient to mechanically ventilate and optionally to sedate a patient. During mechanical ventilation, the ventilator feeds a breathing gas to the patient via the fluid connection, and the exhaled breathing gas is led away from the patient. The ventilator may be configured as an anesthesia apparatus, which adds an anesthetic to the breathing gas being fed to the patient. The exhaled air, which may contain anesthetic in one embodiment, is optionally fed again to the ventilator, so that a ventilation circuit is generated.

In order to be able to carry out the mechanical ventilation automatically to the extent desired, it is necessary to measure the concentrations of a plurality of gases in the ventilation circuit, especially the concentrations of O2 and CO2, as well as optionally of N2O (nitrous oxide) and/or of at least one anesthetic. As a rule, these gas concentrations are variable over time. The concentration of O2 is especially greater during an inhalation process (inspiration) than during an expiration (exhalation) process (expiration), while the concentration of CO2 is, as a rule, greater during the expiration process than during the inhalation process. An exception may occur when the concentration of a component of the gas mixture, which is being fed to the patient, is rapidly reduced during a mechanical ventilation of the patient. This component is, for example, oxygen or a breathing gas.

One possibility of measuring the gas concentrations which is frequent and is also applied according to the present invention is as follows: A gas sample is suctioned from the ventilation circuit at a branching-off point close to the patient, is fed to a gas sensor array and is subsequently again fed into the ventilation circuit. This branching-off point is embodied, for example, in a Y-piece close to the patient. The gas sensor array measures the sought gas concentrations in the branched-off gas sample. Such a procedure is described, for example, in DE 10 2017 011 625 A1 (corresponding to US2020353197 A1).

A leak may occur between the branching-off point and the gas sensor array, for example, because components, which are being used for the mechanical ventilation or the gas measurement, are not connected to one another in a fluid-tight manner because of an error. Ambient air can be suctioned in due to such a leak. The suctioned-in ambient air may distort the measurement results of the gas sensor array. Hence, detection must be immediate, so that the leak is eliminated or the ventilation is continued without the results of the gas measurement. In particular, a leak has to be immediately detected when at least one parameter of the mechanical ventilation is automatically controlled as a function of the measured concentration of at least one gas or when a user adjusts or changes this parameter as a function of the measured gas concentration.

A plurality of processes and devices have become known for automatically detecting a leak in a fluid connection to a gas sensor array during the mechanical ventilation of a patient.

It is proposed in DE 10 2017 011 625 A1 to measure the time curve (concentration with respect to time) of CO2 and the time curve (concentration with respect to time) of another gas, especially of O2, and to compare the two time curves with one another. In case no leak has occurred, then the two curves are phase-shifted in relation to one another. A statistical indicator of the phase shift between the two curves, especially the covariance, is calculated and compared to a predefined threshold. In case no leak has occurred, then this covariance is ideally −1 and is between −0.6 and −0.8 for all practical purposes.

It is proposed in U.S. Pat. No. 8,033,280 B2 and EP 1961439 A1 to measure the respective time curve of two gases. In case these two time curves move simultaneously in the direction of likewise measured or known gas concentrations in the ambient air, then a leak is detected.

It is proposed in WO 2004/076944 A2 to measure the time curve of a pressure in a patient monitor and the time curve of a pressure in a ventilation circuit and to compare these two time curves with one another.

SUMMARY

A basic object of the present invention is to provide a process for monitoring a measuring system, wherein the measuring system is used for the mechanical ventilation of a patient and a gas sample is suctioned from a fluid connection between the patient and a medical device. The process shall detect a leak automatically and with higher reliability than prior-art processes, wherein the leak to be detected may impair a measurement of the concentration of at least one gas in the suctioned gas sample. Moreover, a basic object of the present invention is to provide such a measuring system. The medical device may comprise one of a ventilator, an anesthesia apparatus and a patient monitor.

Advantageous embodiments of the process according to the present invention are, where meaningful, also advantageous embodiments of the measuring system according to the present invention and vice versa.

The process according to the present invention monitors a measuring system. This measuring system can be used for the mechanical ventilation of a patient. The process for the monitoring is carried out while the patient is being mechanically ventilated. The patient may be fully sedated during the mechanical ventilation. The process according to the present invention can also be used when the mechanical ventilation overlaps a spontaneous breathing (own breathing activity) of the patient.

The measuring system comprises a gas sensor array and a gas sensor fluid-guiding unit. A fluid-guiding unit in the sense of the claims is capable of carrying a fluid from one point to another point, ideally without any fluid leaking or without a gas from the environment being able to enter the interior of the fluid-guiding unit on the path between these two points. The fluid-guiding unit does not necessarily comprise a delivery unit. The fluid-guiding unit is especially a hose, but may also be a tube or a combination of hose and tube. A leak has occurred when gas can enter the fluid-guiding unit and/or gas can be released from the fluid-guiding unit.

The process is carried out while a fluid connection is established between the patient and a medical device. This fluid connection is established by means of a patient-side fluid-guiding unit. The medical device is especially a ventilator or an anesthesia apparatus or a patient monitor. The patient-side fluid-guiding unit connects the patient to the medical device.

The process according to the present invention comprises the following steps, which are carried out automatically:

A gas sample is suctioned from the patient-side fluid-guiding unit.

The suctioned gas sample is sent through the gas sensor fluid-guiding unit to the gas sensor array.

An indicator of the concentration of carbon dioxide ($CO_2$) with respect to time ($CO_2$ concentration time curve) in the suctioned gas sample is calculated.

An indicator of the concentration of another gas with respect to time (other gas concentration time curve) in the suctioned gas sample is calculated. This other gas is different from $CO_2$ and preferably contains oxygen ($O_2$).

The progress over time of the two concentrations (concentration time curves) are calculated using measured values, which the gas sensor array has generated as a function of the suctioned gas sample.

An indicator of a progress over time of the temporal change (the change of the concentration time curve with respect to time—carbon dioxide concentration change curve) of the $CO_2$ concentration is calculated. The change over time of the concentration time curve is the derivative of the concentration time curve.

An indicator of a progress over time of the temporal change (change of the concentration time curve with respect to time—other gas concentration change curve) of the concentration of the other gas, especially the progress over time of the temporal change (change of the concentration time curve with respect to time—concentration change curve) of the $O_2$ concentration, is calculated.

The two concentration time curves are used to calculate these two concentration change curves.

A search is made for any time period with the same sign. A time period with the same sign is a time period, in which the two concentration change curves have the same sign continuously, i.e., throughout the time period, in which concentration change curves are both greater than zero or both less than zero.

When at least one such time period with the same sign is detected, the following steps are carried out:

It is checked whether the two concentration change curves meet a predefined first leak criterion, especially in the detected time period with the same sign or in one or each detected time period with the same sign.

When the first leak criterion is met in at least one checked time period with the same sign, it is decided that a leak has occurred between the patient fluid-guiding unit and the gas sensor array. At least in this case, it is decided that an indicator of such a leak has occurred, and preferably an additional automatic check is then carried out or a check is triggered or an alarm is outputted.

The measuring system according to the present invention comprises the just described gas sensor array, the just described gas sensor fluid-guiding unit and a signal processing unit (with one or more processors and memory—non-volatile memory and/or volatile memory). This signal processing unit is configured to calculate the concentration curves and the concentration change curves, to search for time periods of the concentration change curves with the same sign, to decide whether the first leak criterion is met, and subsequently to decide whether a leak has occurred or there is at least an indication of a leak.

The signal processing unit is thus configured to automatically carry out the steps of the process according to the present invention, in which measured values are analyzed in each case.

According to the present invention, a gas sample is suctioned from the patient fluid-guiding unit and sent through the gas sensor fluid-guiding unit to the gas sensor array. This embodiment makes it possible, on the one hand, to suction the gas sample at a measuring point, which is arranged close to the patient. On the other hand, thanks to the gas sensor fluid-guiding unit, the gas sensor array can be arranged at a distance in space from the patient, for example, in the medical device or in a patient monitor.

The measuring system is in a fluid connection with the patient fluid-guiding unit and is sealed off against the ambient air in a fluid-tight manner when no leak has occurred. The present invention is based on the finding that in case of a leak-free state of the measuring system, the time curve of the $CO_2$ concentration is opposite to the time curve of the concentration of the other gas. Therefore, the time curves of the two changes over time of these concentrations (the concentration change curves) always have the opposite sign, in case no leak has occurred and no other disturbance variable has a significant effect on the time curves. By contrast, a leak establishes a fluid connection between the measuring system and the surrounding area. In case a time period with the same sign of the changes over time of the $CO_2$ concentration and of the other concentration (the concentration change curves) is detected, then according to the present invention, this is an indicator that a leak has occurred.

According to the present invention, the first leak criterion depends on the two concentration change curves in the detected time period with the same sign or in each detected time period with the same sign. This first leak criterion depends markedly less, ideally not at all, on an absolute value of a gas concentration or of a gas pressure. As a result, this first leak criterion is less sensitive than other possible leak criteria to adjustments during the mechanical ventilation and disturbance variables and hence in many cases yields fewer nuisance alarms with approximately equal reliability.

The first leak criterion can be configured such that, on the one hand, any leak—or at least any leak that could have a considerable effect on the measurement of the gas concentrations—is detected with sufficiently high reliability, and only relatively few nuisance alarms are generated, on the other hand.

The feature that time periods with the same sign are detected as a function of the two concentration change curves eliminates the need to detect a leak as a function of a comparison of a calculated parameter value with a predefined threshold value or with a reference parameter value calculated beforehand. Rather, the first leak criterion is based on changes over time of concentrations. Especially because of this, by applying the first leak criterion according to the present invention, a leak can also be detected with relatively high reliability when this leak does not occur suddenly, but rather gradually, for example, because of material fatigue. Just such a gradually occurring leak can often not be detected by a visual inspection and also often not automatically when applying other possible leak criteria.

Moreover, the process according to the present invention and the measuring system according to the present invention do not require that reference measured values be present in case of a guaranteed leak-free state to be able to compare current measured values with these reference measured values obtained during the leak-free state. Rather, the present invention is also capable of detecting a leak when the leak is already present at the beginning of the measurement, for example, because the components of a ventilation circuit are connected to one another incorrectly and therefore not in a fluid-tight manner or because material fatigue is already present at the start of the measurement.

The present invention may in many cases be integrated into an already present measuring system, preferably by suitable software being implemented on a signal processing unit of the measuring system. The sensors needed for the CO2 concentration and for the concentration of the other gas as well as optionally a sensor for the pressure in the gas sensor array and/or a sensor for the ambient pressure, and often the signal processing unit as well are, as a result, already present. The present invention does not need any additional sensors.

The present invention can be used in combination with an embodiment, in which the gas sensor fluid-guiding unit is separated from time to time from the patient fluid-guiding unit, so that no gas sample can flow from the patient fluid-guiding unit to the gas sensor array, and in which a search is made for a leak in this state. However, the present invention does not require that the gas sensor fluid-guiding unit be separated from time to time to search for a leak. Hence, the two processes, measuring gas concentrations and monitoring the measuring system for a leak, can be carried out overlapping in terms of time and especially continuously without interruption. The automatic monitoring for leaks according to the present invention can hence be carried out while a patient is being mechanically ventilated.

Measured values of the gas sensor array are used according to the present invention to calculate the time curves of CO2 and of at least one other gas and, using the time curves, to decide whether or not a leak is present. It is possible that the time curves are additionally used for the mechanical ventilation of the patient, e.g., in order to activate a ventilator and/or in order to measure the spontaneous breathing of the patient. It is possible that the time curves of CO2 and of at least two other gases are calculated, e.g., of O2, N2O and of at least one anesthetic.

Different parameters on which the first leak criterion depends can be predefined. These parameters can be predefined such that the number of nuisance alarms remains relatively low and nevertheless an actually occurred leak is detected with high reliability.

As a rule, the CO2 concentration in the exhaled breathing gas is greater than the CO2 concentration in the breathing gas that is inhaled and/or is fed from a ventilator or anesthesia apparatus. In one embodiment, therefore, any time period, in which the patient exhales breathing gas, is detected. Compared with other time periods, during such an exhalation time period, a leak leads, as a rule, to a greater reduction of the CO2 concentration. Only in such an exhalation time period, a search is preferably made for time periods with the same sign. Compared with an embodiment, in which a search is always made for time periods with the same sign, this embodiment saves calculation time and/or calculation capacity. Because no perceived leak can be detected outside an exhalation time period, the risk of nuisance alarms is reduced.

According to the present invention, the time curve of the CO2 concentration as well as the time curve of the concentration of the other gas in the suctioned gas sample are measured. This other gas is different from CO2 and especially contains oxygen (O2), nitrous oxide (N2O) or an anesthetic. It is possible to expand the process to the concentrations of three different gases.

In one embodiment, a leak is detected when a second predefined leak criterion is met. The second leak criterion depends, on the one hand, on the change over time of an indicator of the phase shift between the two concentration time curves and, on the other hand, on the change over time of a pressure in the gas sensor array or upstream of the gas sensor array. The indicator of the phase shift is preferably calculated by applying a statistical process, especially preferably as a covariance. The second leak criterion also does not require that a measured parameter value be compared with a threshold value or with a reference parameter value measured beforehand.

The second leak criterion is based on the finding that a leak, especially a leak occurring suddenly, leads, as a rule, both to a change in the phase shift and to a change in the pressure in the measuring system, especially to a change in the measured pressure in relation to the ambient pressure. The second leak criterion is based on these two consequences of a leak. The second leak criterion is able to detect suddenly occurring leaks with higher reliability than other possible leak criteria.

A process for detecting a leak can be carried out exclusively based on the second leak criterion, wherein a gas sample is suctioned out and wherein the indicator of the phase shift as well as the change over time of the pressure curve are measured, but wherein a search for time periods with the same sign is not necessarily made and wherein the first leak criterion is not necessarily used.

In one preferred embodiment, a mean pressure in the measuring system is determined, for example, averaged over a complete breathing phase (breath) or an inhalation phase or an exhalation phase of the patient. The change over time of this mean pressure is used for the second leak criterion. By using an averaged pressure, random fluctuations in the pressure are eliminated by calculation. By contrast, a leak brings about a systematic change in pressure, which leads to a change over time of the mean pressure.

By contrast, in one preferred embodiment, a leak—or an indication of a leak—is detected when the first leak criterion, the second leak criterion or both leak criteria are met. This embodiment makes it possible to detect with relatively high reliability both a slowly developing leak by means of the first leak criterion and a suddenly occurring leak by means of the second leak criterion. In many cases, a suddenly occurring leak leads to both leak criteria being met.

When the second leak criterion is used, a time shift is predefined. In one embodiment this time shift depends on the interval between the measuring point, at which the gas concentrations are measured, and the measuring point, at which the pressure is measured, and optionally in addition, on the flow rate of a gas, while the gas flows from one measuring point to the other measuring point. This predefined time shift takes into consideration the following fact: When the gas concentrations and the pressure are measured at different measuring points, a suddenly occurring leak leads to a time delay between the change in the pressure and the change in the phase shift.

In another embodiment, this time shift depends on the phase shift between the curve of the CO2 concentration and the curve of the concentration of the other gas.

As already stated, the present invention pertains to a measuring system, which can be used for the mechanical ventilation of a patient. In one embodiment, this measuring system is a component of a connection device, which comprises, in addition, a patient fluid-guiding unit. A fluid connection can be established between a patient and a medical device by means of this patient fluid-guiding unit. The gas sensor fluid-guiding unit of the measuring system according to the present invention is connected to the patient fluid-guiding unit at least from time to time.

The measuring system preferably generates an alarm and transmits this alarm to a receiver located at a distance in space and/or outputs this alarm in a manner perceptible to a person when a leak is detected. In one embodiment, the measuring system generates the alarm already when the first leak criterion and/or the second leak criterion are met.

In another embodiment, the measuring system first carries out a check when the first leak criterion or optionally at least one leak criterion is met. For this check, the step of suctioning a gas sample from the patient fluid-guiding unit is temporarily interrupted. By contrast, gas preferably continues to flow through the patient fluid-guiding unit because the mechanical ventilation of the patient is being continued. During this interruption. the pressure in or at the measuring system as well as the pressure in the patient fluid-guiding unit are each measured at least once, and the measured pressures are compared with one another. In case a leak has actually occurred, then the pressure in or at the measuring system deviates significantly from the pressure in the patient fluid-guiding unit. At least in one inhalation time period, the pressure in the measuring system is, as a rule, lower than in the patient fluid-guiding unit because of a leak. An alarm is generated in this case. Due to this check, the number of nuisance alarms can be further reduced, wherein it is guaranteed at the same time that, as a rule, an actually occurring leak is detected.

In another embodiment, the present invention pertains to a medical system. This medical system comprises a medical device, especially a ventilator or an anesthesia apparatus or a patient monitor, as well as the just described connection device with the measuring system according to the present invention. The connection device is capable of establishing a fluid connection between the medical device and a patient at least from time to time.

The medical device is preferably capable of receiving the time curve of the CO2 concentration and the time curve of the other gas or of at least one other gas. These at least two time curves were calculated by the signal processing unit of the measuring system, for which the signal processing unit uses measured values from the gas sensor array. In one embodiment, the medical system is capable of automatically processing the received time curves, for example, in order to actuate an actuator, which generates ventilation strokes. In one embodiment, the medical device is capable of outputting the received time curves in a manner perceptible to a person, preferably graphically on an output unit.

In one embodiment, the signal processing unit of the measuring system according to the present invention is a component of the medical device. It may be separated at a space from the medical device as well.

The present invention will be described below on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
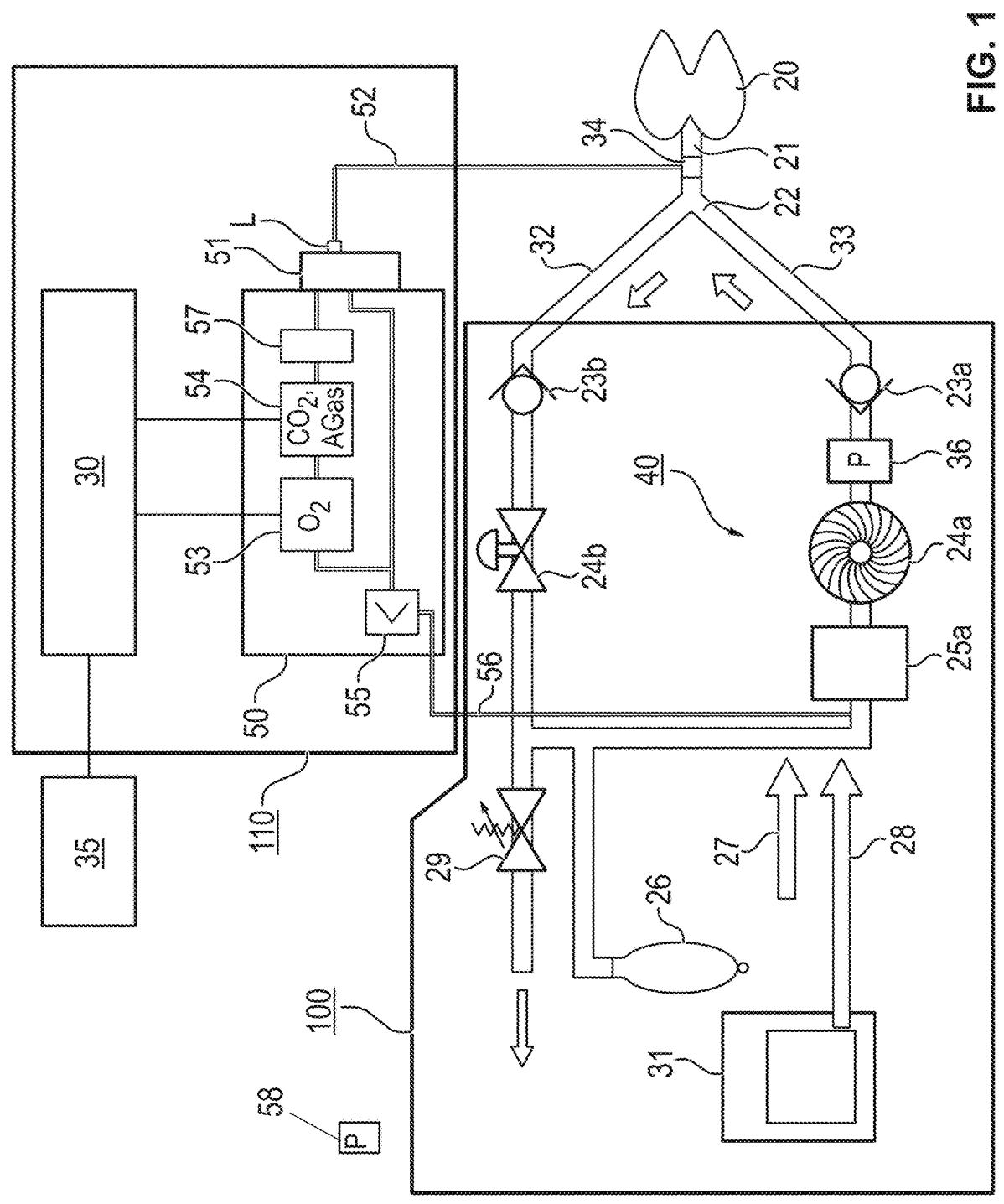
FIG. 1 is a schematic view showing a ventilation circuit for the mechanical ventilation of a patient.

Referring to the drawings, FIG. 1 schematically shows a ventilation circuit 40 to mechanically ventilate a patient 20. It is possible that the ventilation circuit 40 feeds an anesthetic to the patient 20, so that the patient 20 is partly or fully sedated. The present invention can also be used in a ventilation circuit 40, in which the patient 20 is mechanically ventilated, but no anesthetic is fed to the patient 20. It is possible that the mechanical ventilation and the spontaneous breathing of the patient 20 overlap.

A patient-side coupling unit 21, for example, a mouthpiece or breathing mask, connects the patient 20 to the ventilation circuit 40. The mouthpiece 21 is connected to a Y-piece 22. The Y-piece 22 is connected to a breathing gas line 32 for inhalation (inspiration) and to a breathing gas line 33 for exhalation (expiration).

The ventilation circuit 40 connects the patient-side coupling unit 21 to the ventilator 100, which is configured as an anesthesia apparatus in one configuration of the exemplary embodiment. The ventilation circuit 40 is passed through the ventilator 100.

FIG. 1 schematically shows which components described below belong to the ventilator 100 of the exemplary embodiment.

A delivery unit 24a in the form of a pump or of a blower suctions breathing gas and generates a permanent stream of breathing gas through the inhalation breathing gas line 32 toward the Y-piece 22 and toward the patient 20. This delivery unit 24a preferably operates as a compressor, which generates an overpressure and rotates with a speed of over 10,000 rpm. A carbon dioxide absorber 25a is capable of absorbing carbon dioxide from the ventilation circuit 40. A nonreturn valve 23a lets a gas flow in the inhalation breathing gas line 32 pass to the Y-piece 22 and blocks a gas flow in the reverse direction.

A nonreturn valve 23b lets a gas flow in the exhalation breathing gas line 33 pass from the Y-piece 22 and blocks a gas flow in the reverse direction. An actuatable PEEP valve 24b (PEEP="positive end-expiratory pressure") lets, depending on the position, the air stream, which the delivery unit 24a has generated, pass or blocks it and as a result generates the individual ventilation strokes and fixes the amplitudes and frequencies of these ventilation strokes. The PEEP valve 24b ensures, in addition, that a sufficiently high air pressure is also maintained in the lungs of the patient 20 at the end of the exhalation or during a brief opening or interruption of the ventilation circuit 40. An overpressure valve 29 is capable of lowering an overpressure in the ventilation circuit 40 by breathing gas being released into the surrounding area. This overpressure valve 29 is preferably configured as an "adjustable pressure limiting valve" and reduces the risk that the lungs of the patient 20 are damaged, especially in case of a manual ventilation by means of a breathing bag 26. The pressure limit at which this overpressure valve 29 opens can be adjusted manually from outside and/or automatically by an actuation of the overpressure valve 29.

An optional anesthetic vaporizer 31 is capable of feeding a fluid stream 28 with a mixture in vapor form of a carrier gas and at least one anesthetic into the ventilation circuit 40. In addition, a fluid stream 27 of fresh air or of another fresh gas can be fed to the ventilation circuit 40.

The ventilation circuit 40 is kept running by the delivery unit 24a and optionally by a breathing bag 26, which can be actuated manually.

The delivery unit 24a, the optional anesthetic vaporizer 31, the carbon dioxide absorber 25a, the nonreturn valves 23a and 23b as well as the valves 24b and 29 belong to the schematically shown ventilator 100, which can be configured as an anesthesia apparatus. It is also possible that the ventilation circuit 40 is kept running exclusively by means of the breathing bag 26, for example, onboard a vehicle or at another location, at which no stationary power supply is available, or the power supply has failed, or the delivery unit 24a has broken down.

A control device 35 receives measured values from a pressure sensor 58, which measures the air pressure $P_{amb}$ in the surrounding area of the ventilator 100. In addition, the control device 35 receives measured values from a pressure sensor 36, which measures the current pressure in the ventilation circuit 40, for example, the ventilation pressure (airway pressure, $P_{aw}$) present at the patient 20, preferably as pressure in relation to the ambient pressure $P_{amb}$. The control device 35 actuates the delivery unit 24a, the anesthetic vaporizer 31 and other components of the ventilator 100, in order to achieve a desired ventilation of the patient 20. The control device 35 comprises one or more processors and memory—non-volatile memory and/or volatile memory.

For the actuation of the ventilator 100, it is necessary that the actual current concentration of carbon dioxide (CO2), oxygen (O2), nitrous oxide (N2O) and optionally a fed-in anesthetic be measured, especially the concentrations close to the patient-side coupling unit 21 and thus close to the mouth and/or close to the nose of the patient 20.

For this purpose, a sample containing breathing gas is taken (branched off) via a gas sensor fluid-guiding unit in the form of a removal hose 52 from the ventilation circuit 40 and fed again into the ventilation circuit 40 via a discharge hose 56. The removal hose 52 begins in a branching-off point 34 between the patient-side coupling unit 21 and the Y-piece 22. Optionally, a valve, not shown, that separates the removal hose 52 from the ventilation circuit 40 in the closed position and that can be actuated by the control device 35 is located at the branching-off point 34. When the valve is open, the removal hose 52 is in an unrestricted fluid connection with the ventilation circuit 40. The discharge hose 56 leads to a feed point upstream of the carbon dioxide absorber 25a.

The removal hose 52 sends the breathing gas sample to a gas sensor array 50. This gas sensor array 50 is located at a distance in space from the patient-side coupling unit 21 and in one embodiment belongs to the ventilator 100. The gas sensor array 50 comprises a pump 55 that sucks in breathing gas through the removal hose 52. The pump 55 preferably continuously generates a vacuum on the side pointing toward the removal hose 52 and continuously an overpressure on the side pointing toward the discharge hose 56. The pump 55 is capable of generating a volume flow of, for example, 200 mL/min.

A sensor 54 is capable of measuring signals that correlate with the respective concentration of CO2, N2O and anesthetic in the suctioned gas sample. This sensor 54 preferably comprises an infrared measuring head, which utilizes the dipole moment of molecules in the breathing gas sample and quantitatively analyzes the absorption of infrared-active gases in order to determine the respective concentration. A sensor 53 is capable of measuring a signal which correlates with the concentration of O2. It is possible that the gas sensor array 50 comprises additional sensors, especially in order to provide redundancy. In addition, the gas sensor array 50 comprises a pressure sensor 57, which measures the pressure $P_{cell}$ of the breathing gas sample at the inlet of the gas sensor array 50. This pressure $P_{cell}$ is variable over time, because the pressure in the ventilation circuit 40 varies and because the removal hose 52 is in a fluid connection with the ventilation circuit 40 when no valve is present at the branching-off point 34 or as long as the optional valve at the branching-off point 34 is open, so that the pressure in the ventilation circuit 40 travels approximately at the speed of sound to the gas sensor array 50.

In one embodiment, the sensors 53 and 54 measure partial pressures, for example, using optical measuring processes. The pressure sensor 57 measures the entire absolute pressure $P_{cell,abs}$ of the breathing gas sample. The quotient of a partial pressure and the entire absolute pressure $P_{cell,abs}$ yields an indicator of the concentration of a gas in the suctioned gas sample.

The pressure sensor 57 preferably measures an absolute pressure $P_{cell,abs}$. The internal pressure in the gas sensor array 50 in relation to the ambient pressure $P_{amb}$ is used as the pressure $P_{cell}$ below, i.e., $P_{cell}=P_{cell,abs}-P_{amb}$. The relative pressure $P_{cell}$ may therefore also have negative values, namely in case of a vacuum in the gas sensor array 50 in relation to the ambient pressure $P_{amb}$. The relative pressure is preferably measured multiple times during a breathing process. A value, which was calculated by suitable averaging of these measured values obtained during a breathing process, is used as the pressure $P_{cell}$.

A data-processing signal processing unit 30 receives measured values from the sensors of the gas sensor array 50, especially from the CO2, N2O and anesthetic sensor 54, from the O2 sensor 53, from the pressure sensors 57 and 58 and optionally from additional sensors, and then automatically analyzes these measured values. The data-processing signal processing unit 30 comprises one or more processors and memory—non-volatile memory and/or volatile memory. Depending on the measured values received, the signal processing unit 30 generates signals concerning the respective current concentration of O2, CO2, N2O as well as anesthetic and transmits these signals to the control device 35. The control device 35 uses these received signals to actuate actuators of the ventilator 100 and, as a result, to automatically control the ventilation circuit 40.

The breathing gas sample that is preferably suctioned continuously by the pump 55 flows through a water trap 51, which is arranged upstream of the sensors 53 and 54. This water trap 51 is equipped with at least one gas-permeable diaphragm, this diaphragm being preferably made of a chemically inert material, e.g., polytetrafluoroethylene (PTFE). This water trap 51 may be configured, for example, as described in DE 10 2007 046 533 B3 (and corresponding U.S. Pat. No. 8,291,903 (B2)) or in DE 10 2009 024 040 A1 (and corresponding U.S. Pat. No. 8,221,530 (B2)). U.S. Pat. No. 8,291,903 (B2) and U.S. Pat. No. 8,221,530 (B2) are incorporated herein by reference. In this way, the suctioned breathing gas sample is freed from condensate, particles, suspended matter and germs. Liquid, especially condensed water vapor, is retained by the diaphragm and flows into a tank of the water trap 51.

The gas sensor array 50, the water trap 51 and the signal processing unit 30 belong to a measuring system 110, which is schematically shown in FIG. 1.

It is possible that a leak occurs on the path from the branching-off point 34 of the removal hose 52 up to the sensors 54 and 53, for example, because the removal hose 52 is not connected in a fluid-tight manner to the patient-side coupling unit 21, to the Y-piece 22 or to the water trap 51 or because material fatigue or a mechanical action from outside has led to a leak. This leak may occur abruptly, for example, because the mechanical ventilation has begun, even though two parts are incorrectly connected to one another incorrectly in a non-fluid-tight manner, or gradually, for example, because of material fatigue. A leak L in the transition between the removal hose 52 and the water trap 51 is shown as an example in FIG. 1.

Such a leak L may distort the measured results of the sensors 53 and 54 and of optional additional sensors. Then in the removal hose 52 a vacuum in relation to the ambient pressure $P_{amb}$ and also in relation to the pressure $P_{aw}$ occurs in the ventilation circuit 40 at least during the exhalation. This vacuum results from the fact that the measuring system

110 continuously suctions a breathing gas sample, and is, for example, 100 hPa. Therefore, ambient air can be suctioned through this leak L into the removal hose 52 or into the gas sensor array 50. Because the vacuum in the removal hose 52 varies in relation to the ambient pressure $P_{amb}$, the quantity of the ambient air suctioned in also varies over time, as a rule.

The suctioned-in ambient air may simulate an oxygen concentration in the ventilation circuit 40 that is higher than or also lower than the actual oxygen concentration and hence lead to an incorrect measurement. This incorrect measurement may lead to an error during the mechanical ventilation of the patient 20. Hence, a leak L must be detected as quickly as possible, and a corresponding alarm must be outputted in order to be able to rapidly eliminate the leak L. On the other hand, it is desired to generate as few nuisance alarms as possible, ideally no nuisance alarms at all.

Figure 2:
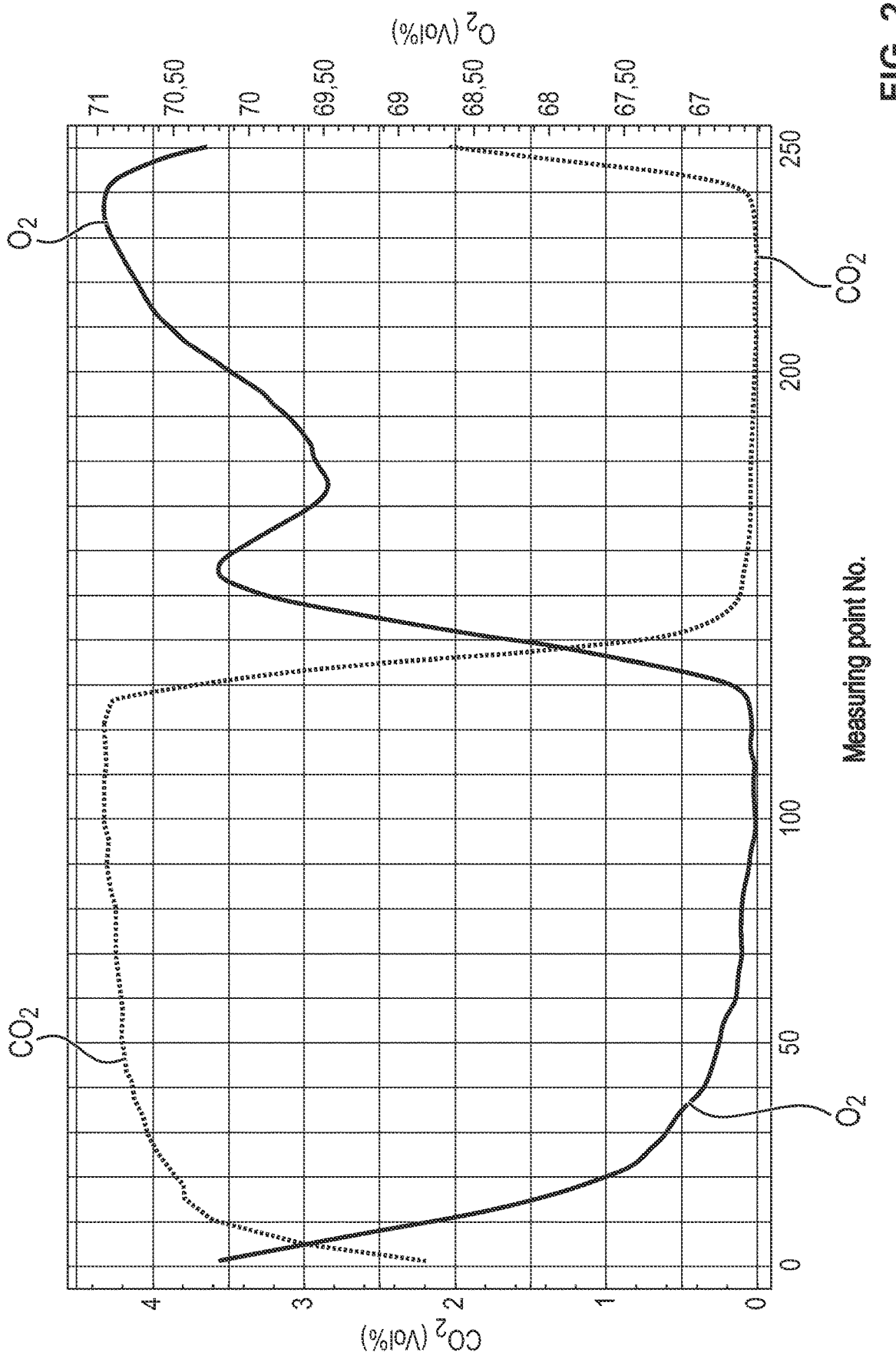
FIG. 2 is a graph showing the change in CO2 concentration with respect to time (CO2 concentration progress over time—the CO2 concentration time curve) and the change in O2 concentration with respect to time (O2 concentration progress with respect to time—the O2 concentration time curve) during a single breath in the absence of a leak.

In case no leak occurs, then the progress over time of the O2 concentration (the O2 concentration with respect to time—O2 concentration time curve) in the ventilation circuit 40 and hence also in the branched-off breathing gas sample is approximately inverted to the progress over time of the CO2 concentration (the CO2 concentration with respect to time—concentration time curve), ideally phase-shifted by half the duration of a breath, in case inhalation and exhalation are of equal duration. During the inhalation, the O2 concentration is markedly higher, and the CO2 concentration is markedly higher, as a rule, during the exhalation. FIG. 2 shows, as an example, the progress over time of the O2 concentration (the O2 concentration with respect to time or O2 concentration time curve) and the progress over time of the CO2 concentration (the CO2 concentration with respect to time or CO2 concentration time curve) during a single breath in a situation, in which no leak has occurred. A scale for time is plotted on the x axis. The sample frequency is thus 50 Hz. The numbers designate the consecutive numbers of the measuring points, wherein the interval between two consecutive measuring points is 20 msec. The left-hand side of the y axis shows a scale for the CO2 concentration in volume %, and the right-hand side of the y axis shows a scale for the O2 concentration in volume %. An expiration process of a breath takes place in the time range of 0 sec up to about 1.3 sec, and an inhalation process of the next breath takes place in the range of 1.3 sec to 2.5 sec.

Figure 3:
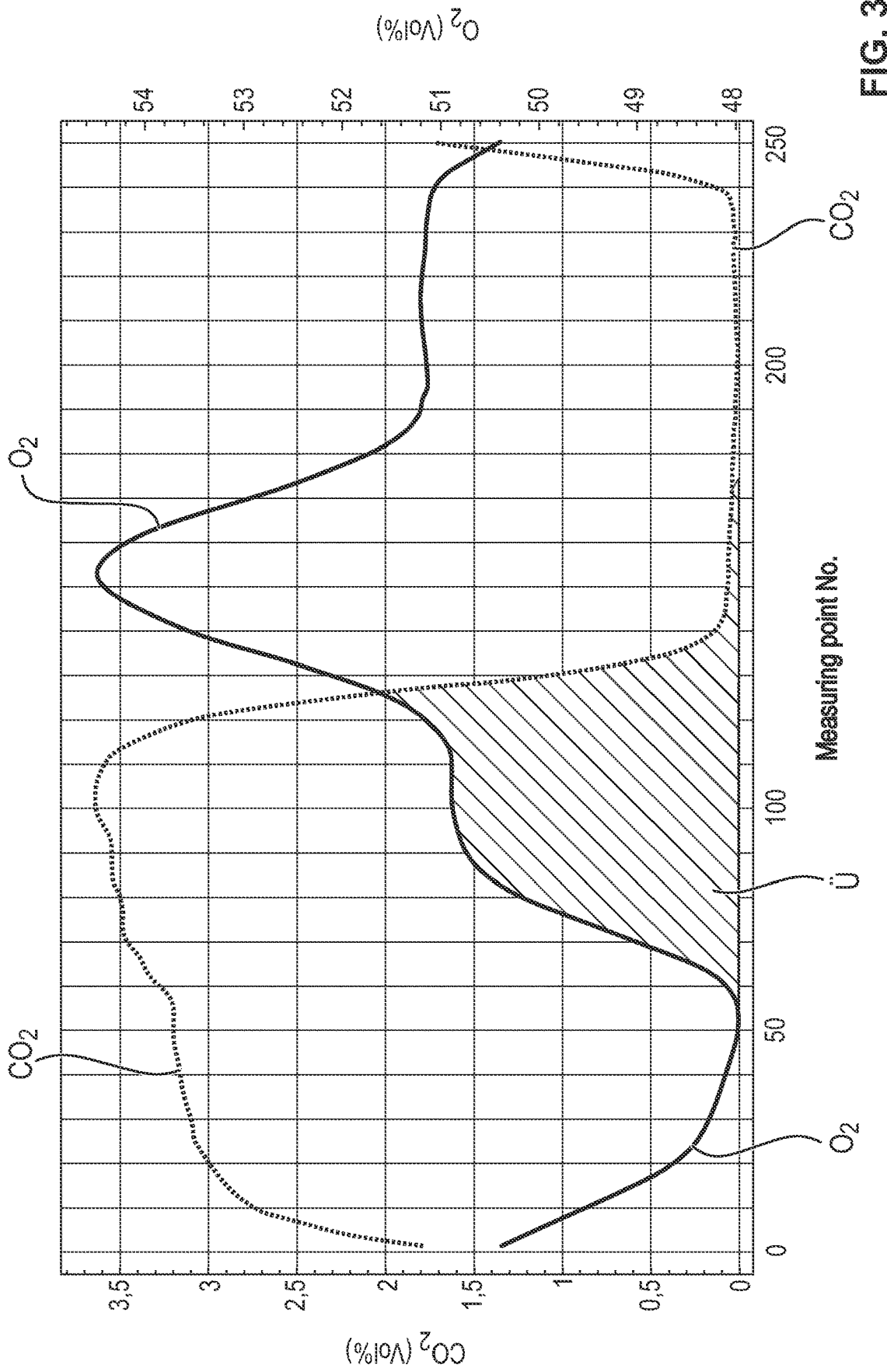
FIG. 3 is a graph showing the time curves of FIG. 2 in the presence of a leak.

FIG. 3 shows the two time curves in the situation of FIG. 2, wherein a leak has occurred in the overall time period from the 1st measuring point up to the 250th measuring point. It can be seen that the two time curves of CO2 and O2 are no longer opposite, but rather a large overlap occurs in the overlapping area Ü.

Figure 4:
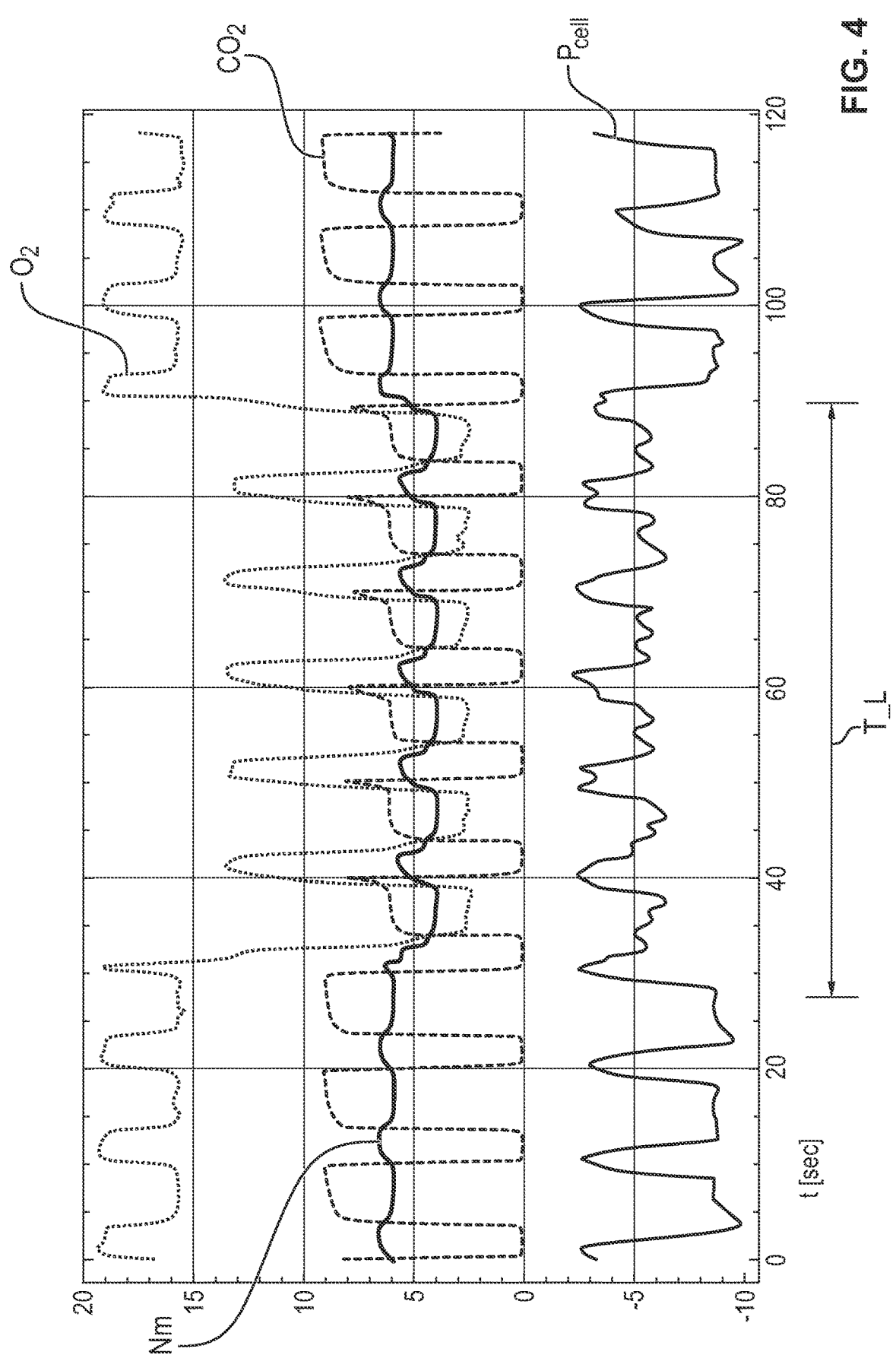
FIG. 4 is a graph showing the scaled time curves of CO2, O2, N2O and anesthetic in the absence and in the presence of a leak.

FIG. 4 shows: the progress over time of the CO2 concentration, the progress over time of the O2 concentration, the progress over time of the concentration of an anesthetic (designated by Nm), and the progress over time of the pressure $P_{cell}$ in a measuring point of the gas sensor array 50.

In the time period of 0 to 120, which is shown in FIG. 4, the pump 55 is switched on continuously and sucks in gas. The four time curves CO2, O2, Nm and $P_{cell}$ were scaled such that they can be shown on the same scale. The time in sec is plotted on the x axis.

It can be seen, on the one hand, that the fluctuations in the concentration of CO2, O2 and Nm follow after the fluctuations in the pressure $P_{cell}$, because the pressure $P_{cell}$ travels approximately at the speed of sound and requires a travel of the variable gas concentrations in the removal hose 52 that is markedly longer than the pressure in order to reach the gas sensor array 50, for example, about 2 sec in case of a 3-m-long removal hose 52.

A leak L has occurred in time period T_L. This leak L leads to a markedly lower O2 concentration and to a somewhat lower CO2 concentration in the time period T_L. In addition, the peaks of the CO2 curve and of the O2 curve change their shapes. The CO2 curve shows in the time period T_L a "peak" per each breath, which occurs in terms of time close to the end of the phase of exhalation. The O2 curve has a rather trapezoidal or rectangular shape.

The signal processing unit 30 determines the respective time curve of the O2 concentration, of the CO2 concentration and optionally also the time curve of the N2O concentration and the time curve of the anesthetic concentration.

The signal processing unit 30 determines each breathing process and the phase of exhalation of this breathing process during the mechanical ventilation of the patient 20 based on the CO2 concentration with respect to time curve and/or on the O2 concentration with respect to time curve. In one embodiment, each phase of exhalation is such a time period between two zero crossings of the standardized CO2 concentration, in which the standardized CO2 concentration is greater than zero, cf. FIGS. 5a and 5b. A measured value CO2(i) and O2(i) for the CO2 concentration and for the O2 concentration at the time t(i) each is present at each sample time t(i) during an expiration process. The respective number of the measuring point is, in turn, plotted on the x axis. The sample frequency is 50 Hz in the example shown.

Figures 5A, 5B:
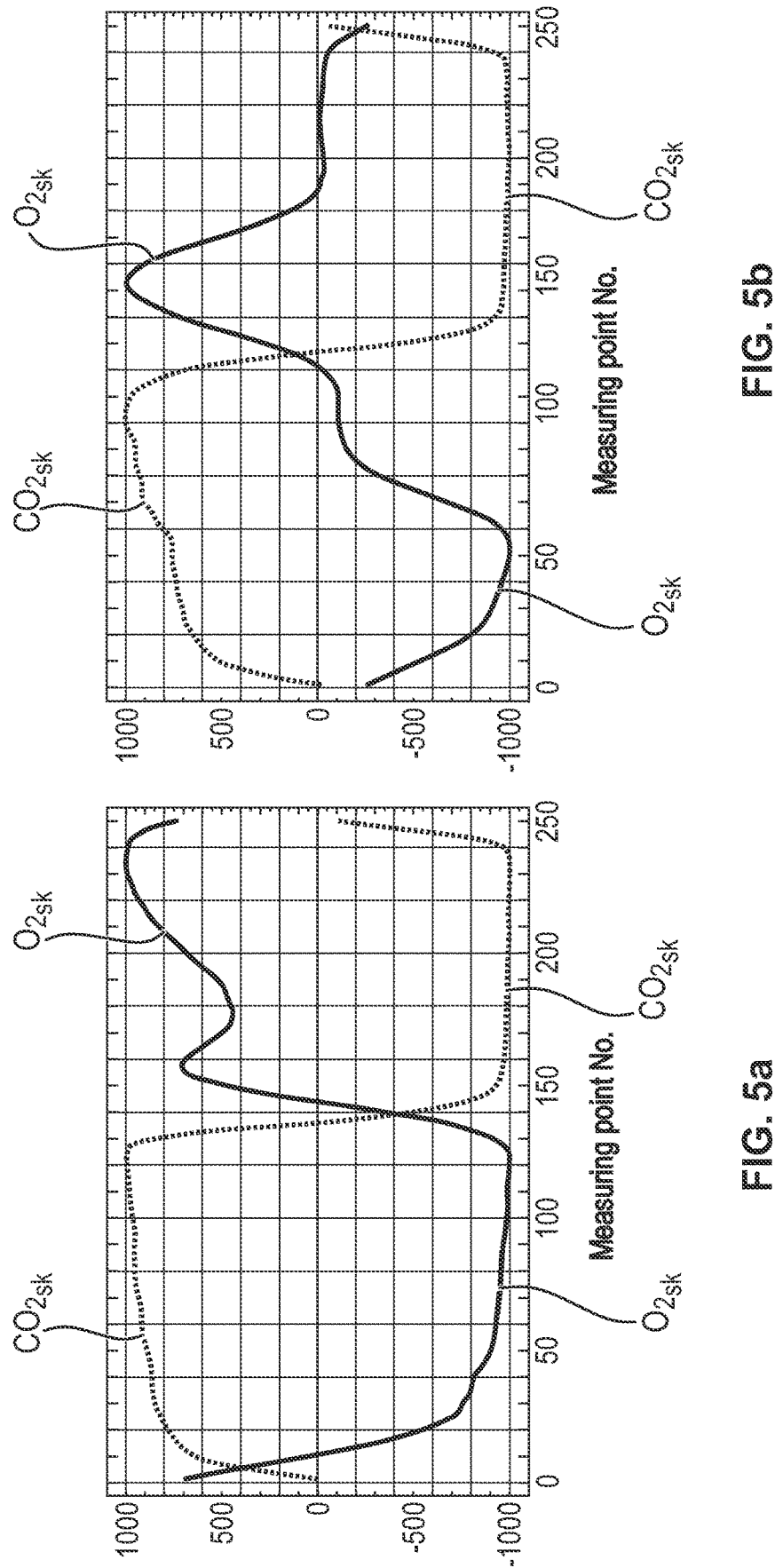
FIG. 5a is a graph showing the CO2 concentration progress over time (CO2 concentration time curve) and O2 concentration progress over time (O2 concentration time curve) of FIG. 2 standardized to a range of −1000 to +1000.
FIG. 5b is a graph showing the CO2 concentration progress over time and O2 concentration progress over time of FIG. 3 standardized to a range of −1000 to +1000.

The signal processing unit 30 standardizes the measured values, which have been measured during an expiration process, to a range between –A and +A, wherein A is a predefined value. For the measured values of the O2 concentration, this standardization is preferably carried out according to the calculation rule $$O2_{sk}(i) = A * \frac{2*O2(i) - [O2_{max} + O2_{min}]}{O2_{max} - O2_{min}}$$

and by means of a corresponding calculation rule for the measured values of the CO2 concentration. Due to this standardization, a constant offset is also eliminated by calculation. In this calculation rule, $O2_{max}$ and $O2_{min}$ designate the largest value and the smallest value, respectively, for the O2 concentration during an expiration process. FIG. 5a shows the standardized curve of the example of FIG. 2. FIG. 5b shows the standardized curve of the example of FIG. 3. A=1000 in this case. Of course, a different value for A and a different calculation rule for the standardization are also possible.

The signal processing unit 30 calculates changes over time in the O2 curve and in the CO2 curve, for example, according to the calculation rule $$\Delta O2_{sk}(i) = O2_{sk}(i) - O2_{sk}(i-s_{O2}) \text{ as well as}$$

$$\Delta CO2_{sk}(i) = CO2_{sk}(i) - CO2_{sk}(i-s_{CO2}),$$

wherein $s_{O2}$ and $s_{CO2} \geq 1$ are two predefined or even calculated numbers (increments). As a result, two difference curves $\Delta O2_{sk}$ and $\Delta CO2_{sk}$ are calculated. The increments (sample size) $s_{O2}$ and scot are preferably between 5 and 50. The sample frequency is, for example, 50 Hz. There is preferably a time period between 5*20 msec=100 msec and 50*20 msec=1 sec between the two sample times i and $i-s_{CO2}$. The changes over time $\Delta O2_{sk}$ and $\Delta CO2_{sk}$ correlate with the derivatives of the concentration curves with respect to time.

The synchronization of the two time curves described below is preferably carried out. It is possible to use different increments $s_{O2}$ and $s_{CO2}$ for O2 and for CO2.

The sample increments $s_{O2}$ and $s_{CO2}$ have an effect on how reliably a leak L is detected and with sufficient certainty can be distinguished from a leak-free state. In one embodiment, experimentally different possible increments $s_{O2}$ and $s_{CO2}$ are tested for the sampled curve of the O2 concentration and for the sampled curve of the CO2 concentration. Which increments $s_{O2}$ and $s_{CO2}$ lead to good detection results may depend on the ventilation rate. It is possible to determine and store in advance one set each of readily suitable increments $s_{O2}$ and $s_{CO2}$ for different values of parameters of the mechanical ventilation. The parameters include especially the rate and the amplitudes of the ventilation strokes as well as ratio of inspiration to expiration over time. When the process shall be carried out, the values of the parameters currently used during the mechanical ventilation are determined, and the associated, stored set of increments $s_{O2}$ and $s_{CO2}$ is used.

In case the two determined and actually used increments are different from one another, a phase shift is brought about, which is preferably offset by calculation. For the offset by calculation, for example, the two difference curves $\Delta O2_{sk}$ and $\Delta CO2_{sk}$ are shifted over time in relation to each other until the minimum of the curve $\Delta CO2_{sk}$ and the maximum of the curve $\Delta O2_{sk}$ are at the same time after the shift.

Such an increment $s_{O2}$ for O2 and such an increment $s_{CO2}$ for O2 are determined and used for the following process, in which the maximum of $\Delta O2_{sk}$, i.e., the maximum of the changes of the standardized O2 values, and the minimum of $\Delta CO2_{sk}$, i.e., the minimum of the changes in the standardized CO2 values, are at the same time, optionally after the just described time shift. The maximum is designated by $\Delta O2_{sk,max}$ and the minimum by $\Delta CO2_{sk,min}$ in FIG. 6.

Subsequently, the signal processing unit 30 calculates for a sequence of sample times during an expiration process a sequence of arithmetic product values according to the calculation rule $$Prod(i) = \Delta O2_{sk}(i) * \Delta CO2_{sk}(i).$$

If no leak L occurs, then, as a result, $\Delta CO2_{sk}(i) > 0$ (CO2 concentration increases) and $\Delta O2_{sk}(i) < 0$ (O2 concentration decreases) apply to each sample time t(i) during an expiration process. As a rule, conversely, $\Delta CO2_{sk}(i) < 0$ and $\Delta O2_{sk}(i) > 0$ apply during an inspiration process. Therefore, Prod (i)<0, as a result, during a full breath, because $\Delta CO2_{sk}(i)$ and $\Delta O2_{sk}(i)$ have different signs, provided no leak L has occurred. By contrast, in case a leak L has occurred, Prod (i)>0, i.e., with the same sign, applies to individual sample times t(i).

Figures 6A, 6B:
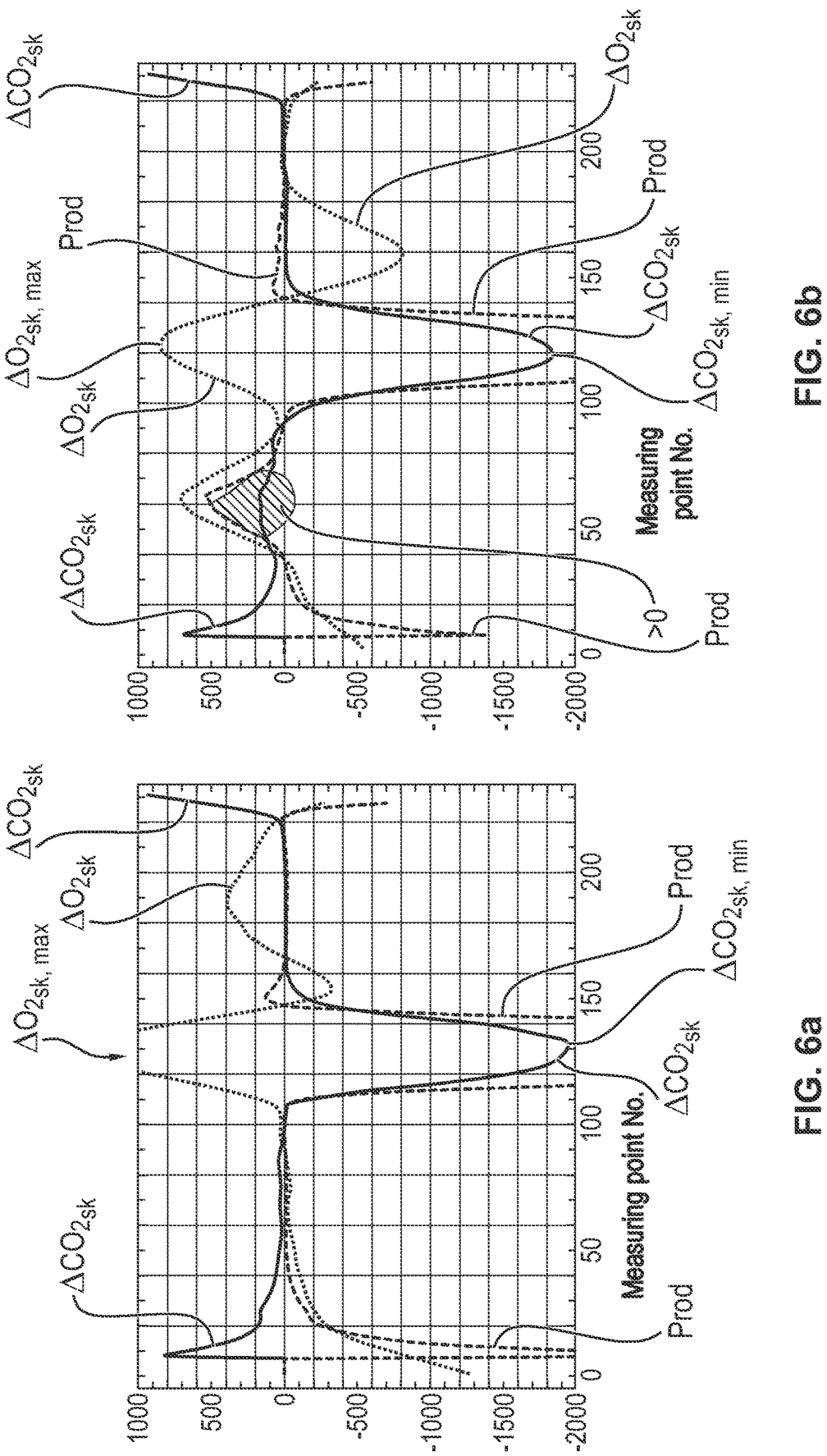
FIG. 6a is a graph showing the progress over time of temporal changes of standardized CO2 and O2 concentration (the changes over time of the standardized CO2 and O2 concentration time curves—concentration change curves) of FIG. 5a as well as the progress over time (time curve) of the product values.
FIG. 6b is a graph showing the progress over time of temporal changes of standardized CO2 and O2 concentration (the changes over time of the standardized CO2 and O2 concentration time curves—concentration change curves) of FIG. 5b as well as the progress over time (time curve) of the product values.

FIG. 6a shows the temporal change of $\Delta CO2_{sk}$, $\Delta O2_{sk}$ and Prod (product value) resulting after the just described synchronization, which result from the example of FIG. 2 (no leak L has occurred). FIG. 6b shows the temporal change of $\Delta CO2_{sk}$, $\Delta O2_{sk}$ and Prod, which result from the example of FIG. 3 (leak L occurred). Furthermore, an area identified by >0, in which Prod(i)>0, is shown in FIG. 6b.

The signal processing unit 30 preferably calculates the product values Prod(i) for each expiration process only, but not for an inspiration process. A leak L has a markedly stronger effect during an expiration process than during an inspiration process, which can be readily seen in FIG. 3. A leak L is also detected rapidly enough in this embodiment, and calculation time is saved. In the example of FIG. 6 an expiration process takes place in the time period between the $1^{st}$ measuring point and the $120^{th}$ measuring point.

A leak L shall be able to be distinguished from other disturbing effects. Such a disturbing effect may result, for example, from the fact that drops of liquid or condensate clog the diaphragm of the water trap 51 until condensed liquid drips into a tank of the water trap 51 or is transported into same and then the diaphragm abruptly has a higher permeability. This abrupt higher permeability could simulate a leak, which is not, in fact, present.

In one embodiment, the signal processing unit 30 calculates the sum DiPhaC of all product values Prod(i) during an expiration process that are greater than 0. DiPhaC means "Differential in Phase Covariance." Except for numerical deviations, this sum DiPhaC is proportional to the surface of the area identified by >0 in FIG. 6*b*. In case this sum DiPhaC is above a predefined threshold, then the signal processing unit 30 has detected a leak L or at least an indication that a leak L has occurred. In one embodiment, the signal processing unit 30 then generates a message that a leak L has been detected.

The just described process with the sum DiPhaC has a plurality of advantages compared with other processes in order to detect a leak L. As long as a leak L occurs, Prod(i) is >0. As soon as the leak L is plugged or is otherwise eliminated, Prod(i) is again <=0. The process with DiPhaC is therefore capable not only of detecting an abruptly occurring leak L, but also a gradually increasing leak L, which may result, for example, from material fatigue. The advantageous effect that different types of leaks can be detected results especially from the fact that the process with DiPhaC does not require comparing a current measured value or a derived value with a reference value, which refers to an earlier sample time.

The process with DiPhaC has, in addition, the following advantage in comparison to the possible procedure of calculating a statistical indicator of the phase shift between the CO2 concentration and the O2 concentration and of comparing this statistical indicator with a limit: The limit, with which the statistical indicator is compared, must be adapted to at least one parameter of the ventilation, for example, to the pressure or to the rate of the mechanical ventilation or to a physiological state of the patient 20. This limit is frequently automatically set as a function of measured values, and these measured values are measured during a leak-free state. The process with DiPhaC does not require such prior knowledge or background knowledge to set a limit and also does not require a leak-free state. Therefore, no initialization phase is needed.

Figure 7:
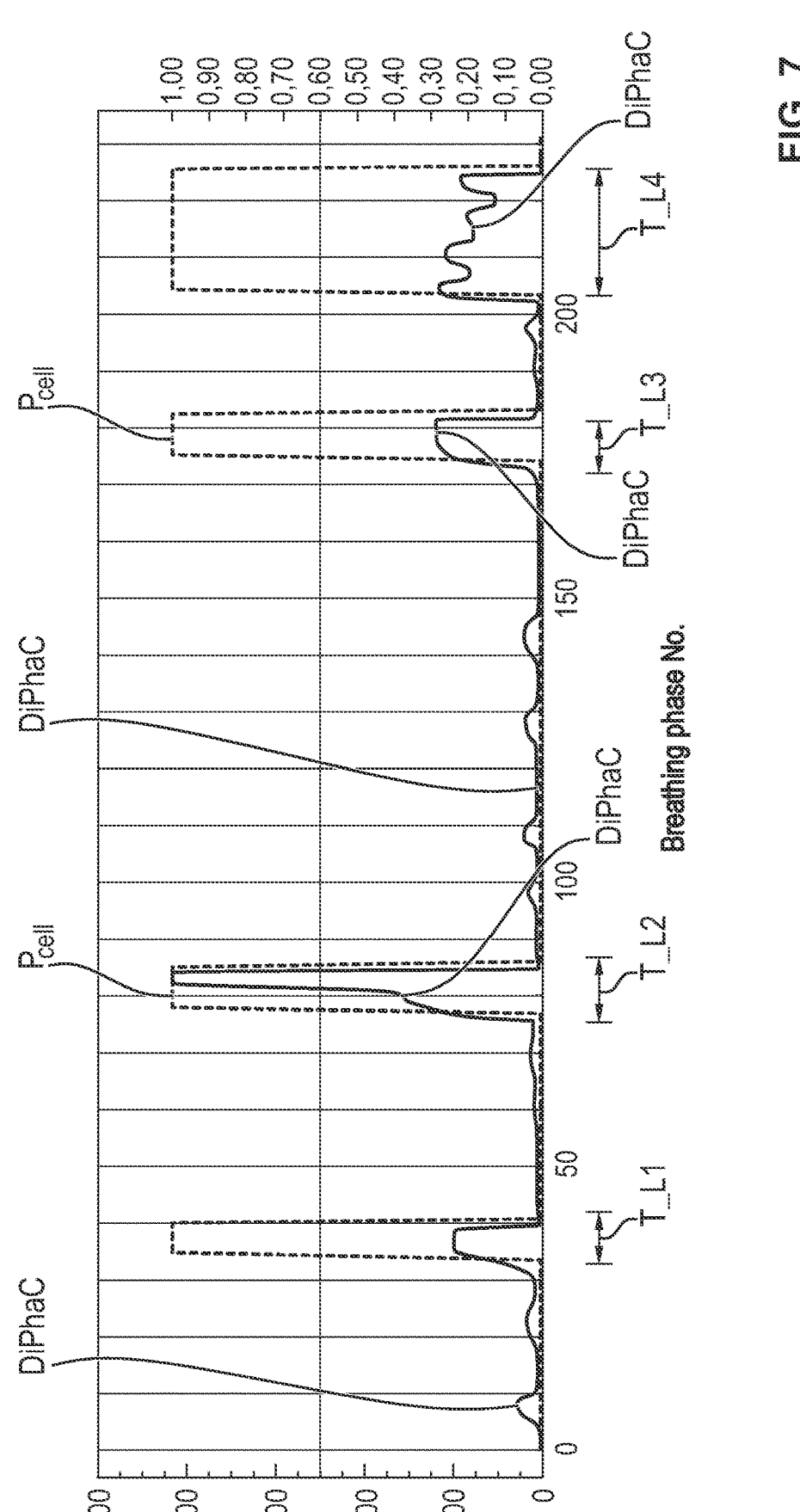
FIG. 7 is a graph showing consequences of leaks which were generated in a test multiple times and again eliminated, and the detection thereof.

FIG. 7 shows the result of a test, in which a leak was generated in a targeted manner. In order to generate a leak L in a targeted manner, an actuatable solenoid valve with a ruby perforated stone was installed in an area at the or close to the inlet of the gas sensor array 50, namely at the point L of FIG. 1. In the fully open position of the solenoid valve, a leak L is created that is so large that the volume flow of the ambient air suctioned through the leak L is about 20% of the entire volume flow of the gas mixture (breathing gas sample and ambient air), which gas mixture flows through the gas sensor array 50. In case such a leak L is not eliminated, the measurement results of the gas sensor array 50 will be considerably distorted.

A leak L was generated in each of the time periods T_Ll, . . . , T_L4. A scale for the position of the valve from 0 (fully closed) to 1 (fully open) is shown on the right-hand side of the y axis. A scale for DiPhaC is shown on the left-hand side of the y axis. The diagram of FIG. 7 shows the time curve (time profile) of the pressure $P_{cell}$ at the gas sensor array 50 and the time curve of DiPhaC. The pressure $P_{cell}$ was averaged over a respective breathing phase of the patient 20, so that each measured value refers to precisely one breathing phase. The consecutive numbers of breathing phases are plotted on the x axis. The duration of a breathing phase may vary over time. $s_{CO2}=26$ and $s_{O2}=25$ were used as exemplary increments for CO2 and O2. It can be seen that a leak L always leads to a value greater than 1000 for DiPhaC, while other effects always lead to a smaller value, namely less than half. Hence, in this case any occurrence of a leak L is detected, and a nuisance alarm is avoided.

The process, which is based on the signal DiPhaC, is preferably complemented by an additional process. Thus, two leak criteria are used, namely DiPhaC as the first leak criterion and a second leak criterion with the designation DPC ("Delta Pressure Covariance"). This additional process is capable with greater certainty of reliably detecting an abruptly occurring leak, especially even with a low or only relatively slightly varying ventilation pressure and/or with a high ventilation rate. A low ventilation pressure or a low amplitude of the ventilation pressure in conjunction with a high ventilation rate are especially used when a child is mechanically ventilated.

The signal processing unit 30 calculates values for the covariance Cov[CO2,O2] between the time curve of the CO2 concentration and the time curve of the O2 concentration multiple times in each case during each phase of exhalation. This covariance Cov[CO2,O2] varies over time. For a plurality of consecutive sample times, the signal processing unit 30 calculates a value for the covariance Cov[CO2,O2] using n respective values for the CO2 concentration and the O2 concentration.

The signal processing unit 30 applies, for example, the following calculation rule:

$$\text{Cov[CO2, O2]}(m) = \frac{2}{n}\sum_{i=1}^{n}\frac{CO2(m+i) - CO2_{avg}}{CO2_{max} - CO2_{min}} * \frac{O2(m+i) - O2_{avg}}{O2_{max} - O2_{min}}$$

In this calculation rule, $O2_{max}$ and $O2_{min}$ designate the largest and the smallest value, . . . , respectively, for the O2 concentration under the n values for the n sample times t(m+1), t(m+n). $O2_{avg}$ designates the arithmetic mean value of these n values. This covariance Cov[CO2,O2] is an indicator of the phase shift between the CO2 concentration, which is variable over time, and the O2 concentration, which is variable over time, in this measuring time period. If no leak has occurred, then the covariance is ideally −1; it is between −0.6 and −0.8 for all practical purposes.

Figure 8:
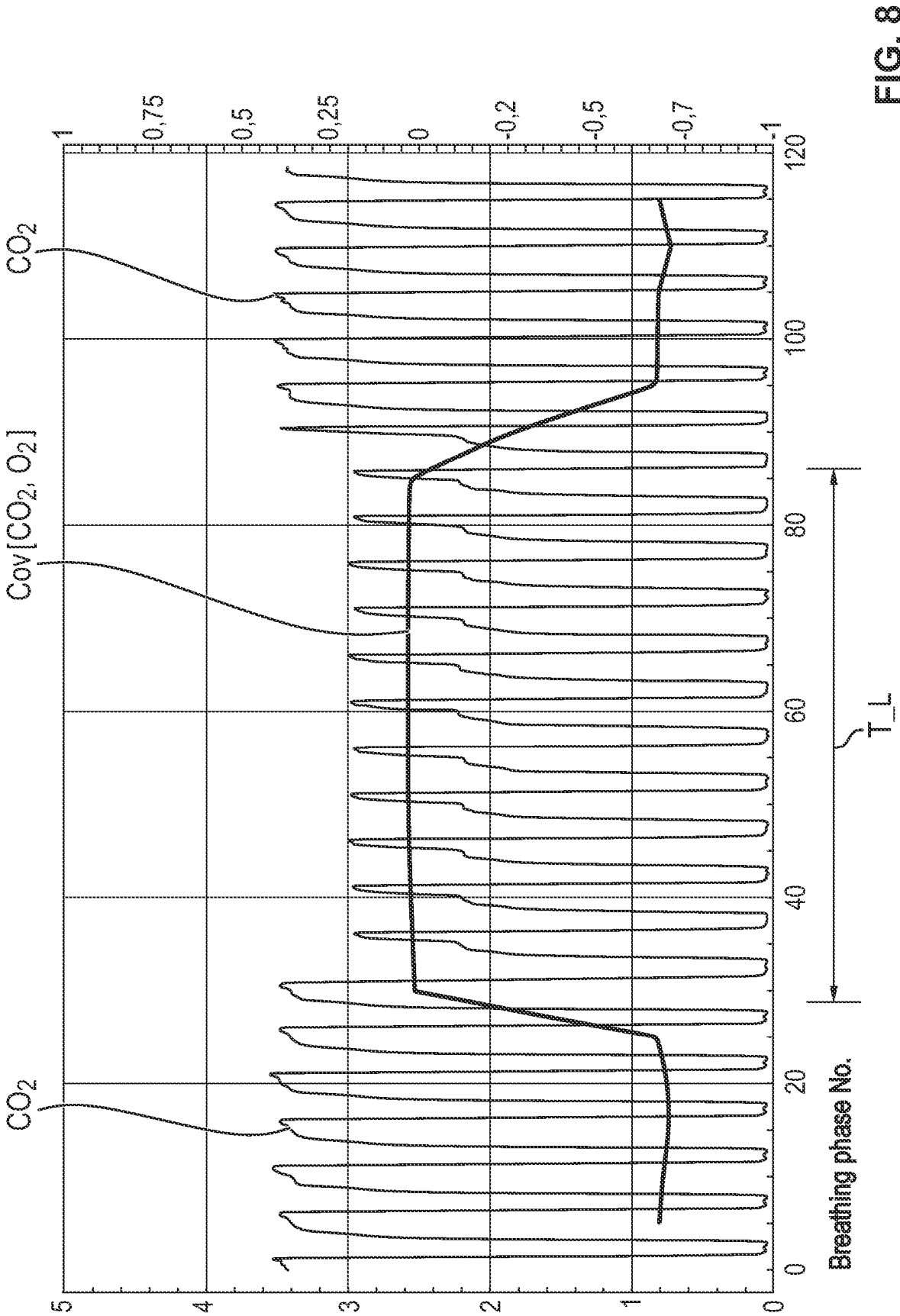
FIG. 8 is a graph showing the progress over time (time curve) of the CO2 concentration and the progress over time (time curve) of the covariance between CO2 and O2.

FIG. 8 shows, as an example, the time curve of the CO2 concentration and the time curve of the covariance Cov [CO2,O2] between CO2 and O2. A scale for the CO2 concentration is plotted on the left-hand side of the y axis, and a scale for the covariance is plotted on the right-hand side of the y axis. The consecutive number of breathing phases is, in turn, plotted on the x axis.

The covariance Cov[CO2,O2]—or another indicator of the phase shift between the two time curves CO2 and O2—is greater in the time period, in which a leak occurs, than in a leak-free time period. However, the value of the covariance Cov[CO2,O2] is not only influenced by the occurrence and the size of the leak L, but also by a variety of other factors, especially by the ventilation pressure, by the ventilation rate and whether the ventilation is carried in a volume-controlled manner or in a pressure-controlled manner.

The procedure described below is in many cases capable of eliminating this drawback, without the consequences of the other factors on the covariance Cov[CO2,O2] having to be known. A basic concept is the procedure of calculating and analyzing the change over time of the covariance. This change in the covariance Cov[CO2,O2] indicates a suddenly occurring leak L.

Furthermore, the signal processing unit 30 calculates a change $$\Delta Cov[CO2,O2](m)=Cov[CO2,O2](m)-Cov[CO2,O2] (m-s_{Cov})$$

of the covariance Cov[CO2,O2] with a predefined increment $s_{Cov}$, for example, $s_{Cov}=1$. Moreover, the signal processing unit 30 calculates a change $$\Delta P_{cell}(j)=P_{cell}(j)-P_{cell}(j-s_{Cell})$$

of the pressure $P_{cell}$. In the example shown, each used value for this pressure $P_{cell}$ is averaged over a respective breathing phase. The sample time t(j) for the pressure $P_{cell}$ is positioned in respect to time in a suitable manner in relation to the covariance Cov[CO2,O2], for example, j=m+n. This positioning in respect to time may depend on the interval between the gas sensor array 50, which measures the concentrations, and a measuring point, at which the pressure sensor 57 measures the pressure, as well as on the flow rate of the suctioned breathing gas sample through the removal hose 52.

The pressure $P_{cell}$ may, for example, change rapidly when a larger quantity of fluid, and especially of condensed water, with the stream of the suctioned breathing gas sample reaches the measuring system 110 and is collected in front of the diaphragm of the water trap 51. When this quantity of fluid flows or is fed abruptly into the tank of the water trap 51, then the diaphragm is released abruptly.

Figure 10:
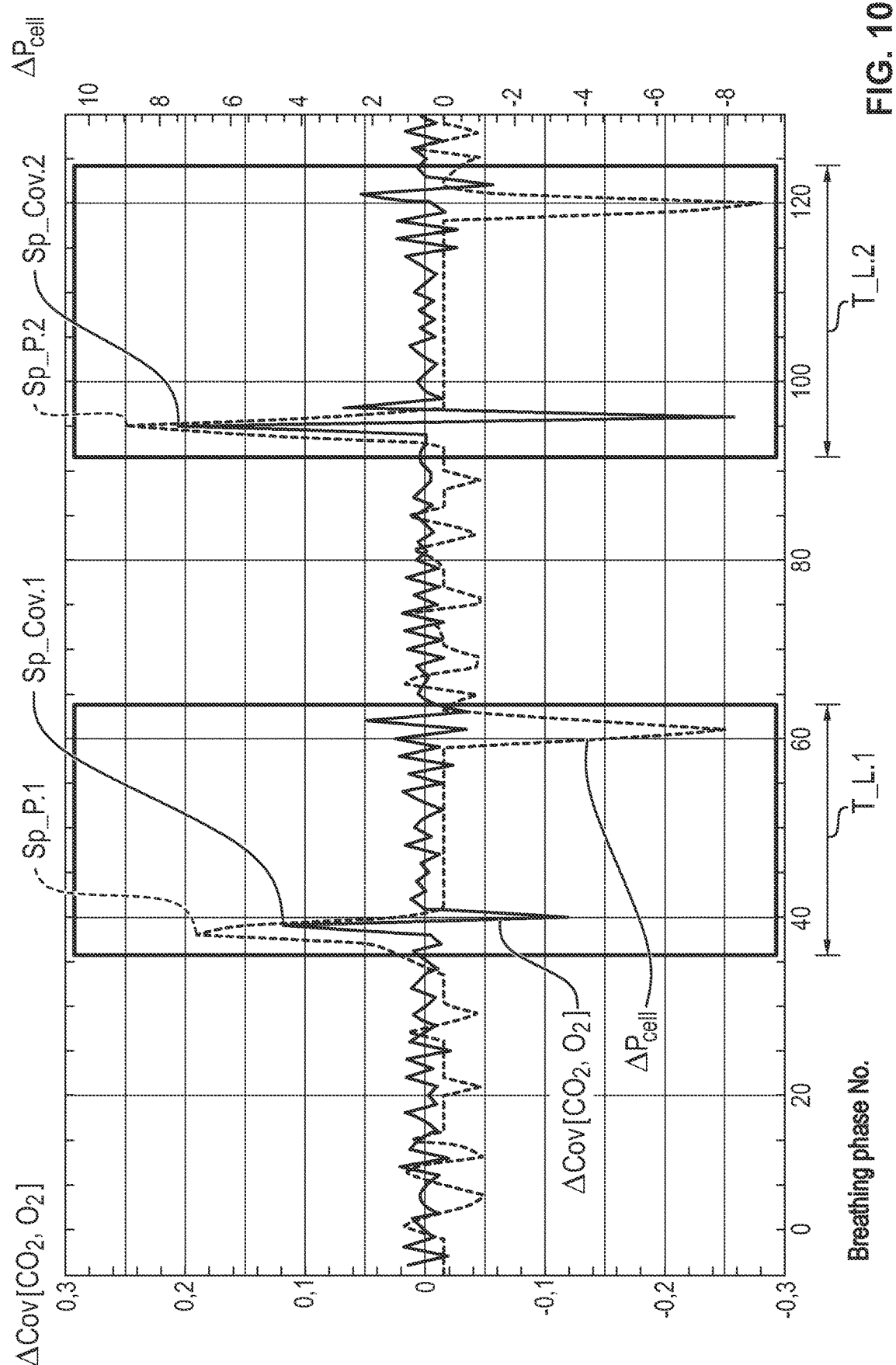
FIG. 10 is a graph showing, as an example, the progress over time (time curve) of $\Delta Cov[CO2,O2]$ and progress over time (time curve) of $\Delta P_{cell}$.

FIG. 10 shows, as an example, the time curves of ΔCov [CO2,O2] and $\Delta P_{Cell}$. The consecutive numbers of the breathing phases of the patient 20 are, in turn, plotted on the x axis. The scale for the dimensionless variable ΔCov[CO2, O2] is plotted on the left-hand side of the y axis, and the scale for the variable $\Delta P_{Cell}$ in hPa is plotted on the right-hand side of the y axis. A leak L has occurred in the two time periods T_L.1 and T_L.2. The first occurrence of the leak L leads to the peak Sp_P.1 of the curve of $\Delta P_{Cell}$ and the peak Sp_Cov.1 of the curve of ΔCov, and the second occurrence leads to the peaks Sp_P.1 and Sp_Cov.1, i.e., to abruptly increasing values. The closing of the leaks L leads to two respective peaks in the opposite direction, i.e., to abruptly decreasing values.

The signal processing unit detects a leak L as a function of the values for ΔCov[CO2,O2] and $\Delta P_{Cell}$. In case, for example, both ΔCov[CO2,O2](j) and $\Delta P_{Cell}$(j) are each above a predefined threshold at a sample time t(j), then a leak L has occurred at this sample time t(j). This process yields a signal, which is designated below as "Delta Pressure Covariance" (DPC). It is also possible to calculate the covariance between ΔCov[CO2,O2] and $\Delta P_{Cell}$. In case this covariance is above a predefined threshold, for example, is greater than 0, then a leak L is detected.

The process with the signal DPC frequently also detects, even in case of low ventilation pressures, i.e., low amplitudes of the CO2 curve and of the O2 curve, as well as at high respiration rates a suddenly occurring leak L in a reliable manner. Only relatively few nuisance alarms are generated, often no nuisance alarms at all.

Both processes DiPhaC and DPC are preferably used in order to detect a leak. A leak L is detected when either DiPhaC or DPC or both criteria generate a signal for the occurrence of a leak L. It is, however, also possible to apply only one of the two criteria.

Figure 9:
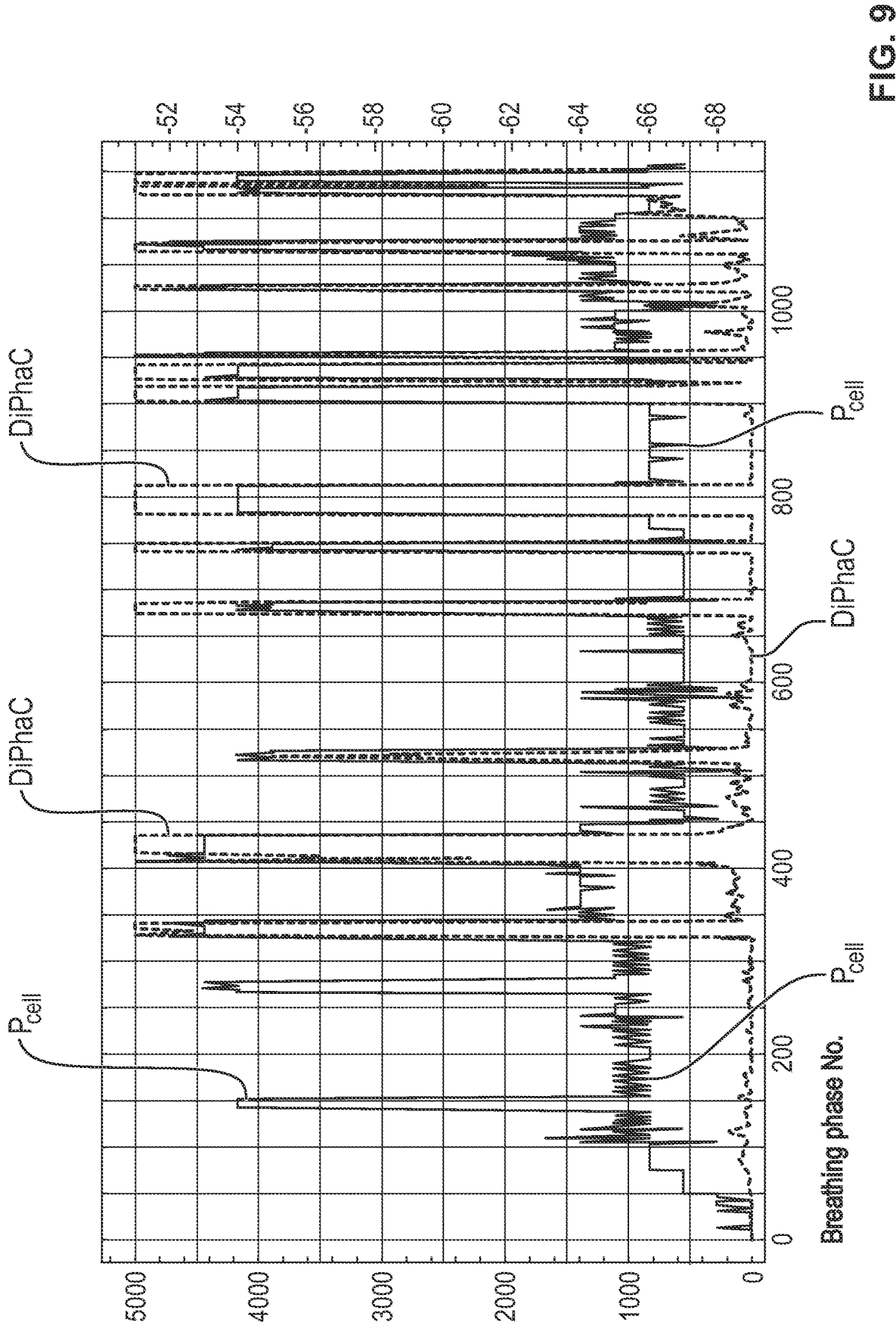
FIG. 9 is a graph showing the progress over time (time curve) of the pressure $P_{cell}$ as well as of the signal DiPhaC in case of a ventilation with high rate and low ventilation pressure.
Figure 11:
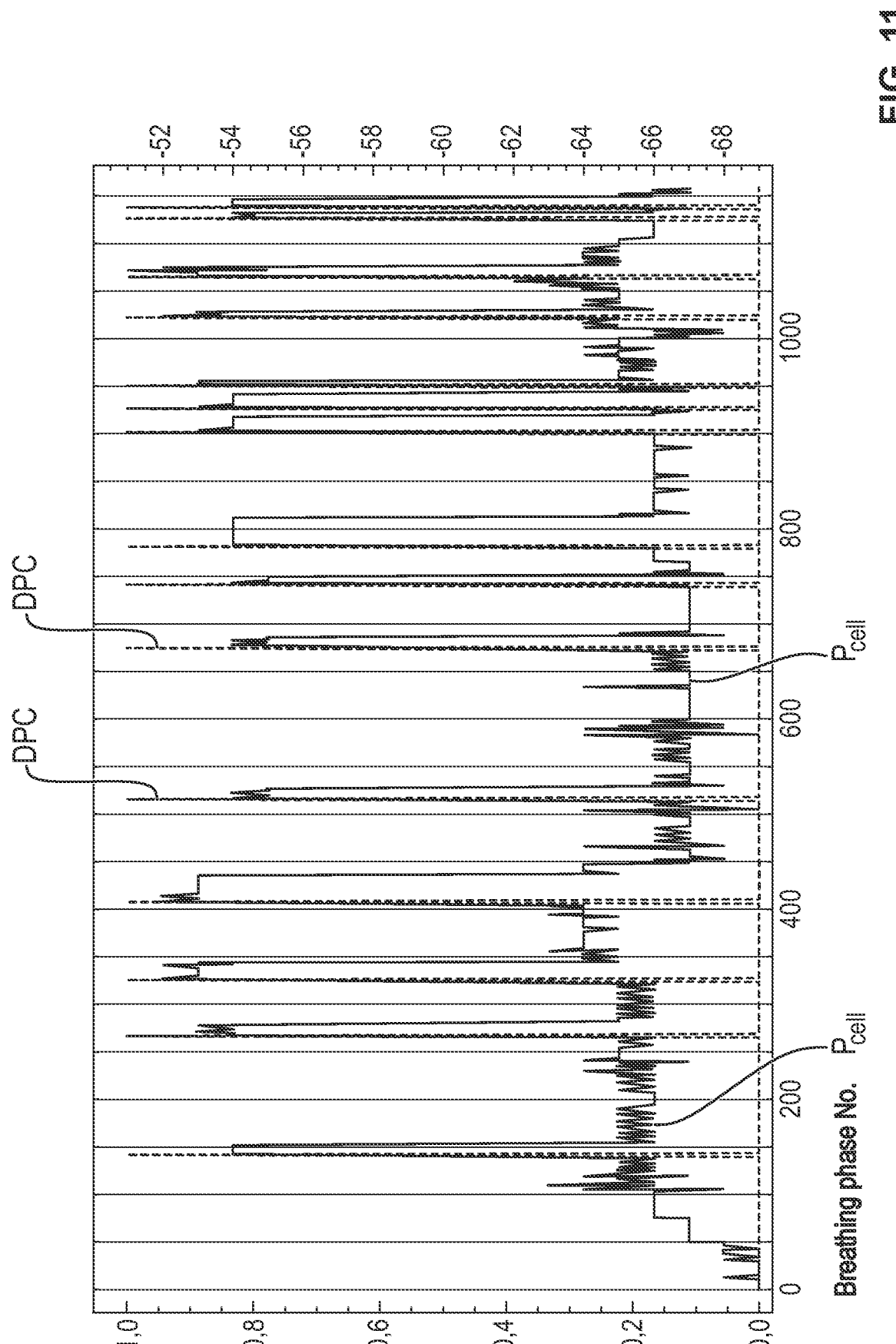
FIG. 11 is a graph showing the progress over time (time curve) of the signal DPC in the situation of FIG. 9.

FIG. 9 and FIG. 11 show the two processes DiPhaC and DPC for detecting a leak L, wherein a patient 20 is mechanically ventilated with a ventilation pressure having a relatively high rate and a relatively low amplitude and wherein a suddenly occurring leak L was generated by tests by means of the above-described solenoid valve 15 times one after the other. FIG. 9 and FIG. 11 each show the curve of the pressure $P_{cell}$ at the inlet of the gas sensor array 50, wherein, in turn, each measured value shown indicates the pressure $P_{cell}$ averaged over a breathing phase of the patient and the consecutive numbers of the breathing phases of the patient 20 are plotted on the x axis. A respective value of the pressure $P_{cell}$ is shown per breathing phase. This shown value is generated, for example, by averaging over a plurality of measured values. The right-hand side of the y axis in both figures indicates the values from −68 to −52 of the pressure $P_{cell}$ in hPa. FIG. 9 shows, furthermore, the time curve of the signal DiPhaC, FIG. 11 shows the signal DPC. The left-hand side of the y axis in both figures shows a scale for this signal. The signal DPC has only the values 0 and 1. In this situation, the process DiPhaC is not capable of detecting the first and the second suddenly occurring leak L, while the process DPC automatically detects all 15 occurring leaks L.

When a leak L has been detected by means of at least one of the processes DiPhaC or DPC, then the gas sensor array 50 transmits a corresponding message to the control device 35. After reception of such a message, the control device 35, in one embodiment, immediately triggers an alarm in a manner perceptible by a person.

In another embodiment, the control device 35, after reception of such a message, first triggers a check whether a leak L has actually occurred that must be eliminated immediately, or else another event that simulates a leak L but does not make any intervention necessary. This check reduces the number of nuisance alarms, without an actually occurring leak L being overlooked. The mechanical ventilation of the patient 20 is continued during this check and is not impaired by the check. In the exemplary embodiment, this check is carried out when the ventilator 100 reaches a positive ventilation pressure above a predefined threshold, i.e., emits breathing gas.

The check whether a leak L has actually occurred comprises in one embodiment the following steps: The pump 55 of the gas sensor array 50 is switched off for the duration of the check. The pressure sensor 58 continues to measure the ambient pressure $P_{amb}$. The pressure sensor 57 of the gas sensor array 50 continues to measure the pressure $P_{cell,abs}$, which is present at the end of the removal hose 52. The pressure sensor 36 in the ventilation circuit 40 continues to measure the pressure in the ventilation circuit 40, for example, the pressure $P_{aw}$.

As is known, the pressure travels at the speed of sound. Except for unavoidable measurement errors and the process noises, the time curve of the pressure $P_{cell}$ in the removal hose 52 coincides with the time curve of the pressure $P_{aw}$ in the ventilation circuit 40, provided no leak has occurred. Because the pump 55 is switched off, a possible clog or other impairment of the diaphragm at the water trap 51 has no effect on the measurement. A reference value, which has been measured before checking for the leak, is not needed.

In one embodiment, the decision whether or not a leak L has actually occurred is made as follows: The pump 55 is switched off. The pressures $P_{Cell}$ in the removal hose 52 and $P_{aw}$ in the ventilation circuit 40 are subsequently compared with one another. For this comparison, the pressure in the ventilation circuit 40, for example, the ventilation pressure $P_{aw}$ present at the patient 20, the pressure $P_{cell,abs}$, which is present at the gas sensor array 50, as well as the ambient pressure $P_{amb}$ are measured at n consecutive sample times $t(1), \ldots, t(n)$. The ambient pressure $P_{amb}$ is measured by the pressure sensor 58 and is especially therefore measured and used, because it may vary over time and this variation over time shall not distort the comparison of relative pressures.

The variable $$\Delta P_{max} = \text{Max}\{P_{aw}[t(1)], \quad . \quad . \quad . \quad , \quad P_{aw}[t(n)]\} - \text{Max}\{P_{cell,abs}[t(1)] - P_{amb}[t(1)], \ldots, P_{cell,abs}[t(n)] - P_{amb}[t(n)]\}$$

is calculated. This variable $\Delta P_{max}$ is ideally equal to the maximum loss of pressure which occurs between the ventilation circuit 40 and the gas sensor array 50 and changes in case of the occurrence of a leak L. A pressure limit $P_{limit}$ is calculated as a function of the ventilation pressure $P_{Insp}$, which the delivery unit 24a generates in the ventilation circuit 40 during the inspiration process, as well as a function of the ventilation rate RR. A leak L is detected when $$\Delta P_{max} > P_{limit}.$$

In case no leak has occurred, then the ambient pressure $P_{amb}$ ideally has no effect on the calculated variable, and $$\Delta P_{max} = 0.$$

The just described procedure takes into account the ambient pressure $P_{amb}$, which has a significant effect on the calculated variable $\Delta P_{max}$ only in case of a leak L, and hence is able to distinguish a leak L from a disturbance variable better than other processes.

While specific embodiments of the invention have been shown and described in detail to illustrate the application of the principles of the invention, it will be understood that the invention may be embodied otherwise without departing from such principles.

LIST OF REFERENCE CHARACTERS

| | |
|---|---|
| 20 | Patient, who is mechanically ventilated, connected to the coupling unit 21 on the patient side |
| 21 | Patient-side coupling unit in the form of a mouthpiece or a breathing mask, connected to the Y-piece 22 |
| 22 | Y-piece, which connects the patient-side coupling unit 21 to a feed line for the feed of gas (inhalation, inspiration) and a discharge line for the discharge of gas (exhalation, expiration) |
| 23a | Nonreturn valve, which lets through a gas flow in the direction of the patient 20 in the inhalation line 32 and blocks same in the opposite direction |
| 23b | Nonreturn valve, which lets through a gas flow away from the patient 20 in the exhalation line 33 and blocks same in the direction toward the patient 20 |
| 24a | Delivery unit, which generates a volume flow in the direction of the patient 20 |
| 24b | PEEP valve, which maintains a pressure in the lungs of the patient 20 |
| 25a | Carbon dioxide absorber, absorbs carbon dioxide from the ventilation circuit 40 |
| 26 | Manual ventilation bag, via which the ventilation circuit 40 can be driven |
| 27 | Fluid stream of fresh air or other fresh gas to the ventilation circuit 40 |
| 28 | Fluid stream of anesthetic in vapor form to the ventilation circuit 40 |
| 29 | Adjustable overpressure valve, which is capable of releasing gas from the ventilation circuit 40 |
| 30 | Data-processing signal processing unit for the gas sensor array 50, analyzes signals from the sensors 53, 54, 57 and 58, is capable of detecting a leak L and of transmitting a message to the control device 35 |
| 31 | Anesthetic vaporizer, generates the anesthesia stream 28 |
| 32 | Breathing gas line for inhalation, connected to the Y-piece 22, has the nonreturn valve 23a |
| 33 | Breathing gas line for exhalation, connected to the Y-piece 22, has the nonreturn valve 23b |
| 34 | Branching-off point of the removal hose 52 |
| 35 | Control device, actuates the delivery unit 24a and the anesthetic vaporizer 31, receives signals about the respective gas concentration and messages from the signal processing unit 30, generates an alarm about a leak L that has occurred, as needed |
| 36 | Pressure sensor in the ventilation circuit 40, preferably measures the pressure $P_{aw}$ present at the patient 20 |
| 40 | Ventilation circuit, through which the patient 20 is mechanically ventilated and sedated, connects the patient 20 to the ventilator 100, comprises the patient-side coupling unit 21, the Y-piece 22, the inhalation line 32 and the exhalation line 33 |
| 50 | Gas sensor array, which measures the concentration of O2, CO2, N2O and anesthetic, comprises the gas sensors 53 and 54, the pump 55 as well as the pressure sensor 57 |
| 51 | Water trap upstream of the gas sensor array 50, comprises at least one diaphragm, which is preferably made of PTFE, and a tank |
| 52 | Removal hose, through which a breathing gas sample is taken from the ventilation circuit 40, begins in a branching-off point 34 between the patient-side coupling unit 21 and the Y-piece 22 and leads to the water trap 51 |

-continued

| 53 | Sensor for the O2 concentration in the breathing gas sample |
| 54 | Sensor for the concentration of CO2, N2O and anesthetic in the breathing gas sample |
| 55 | Pump, which suctions a breathing gas sample into the removal hose 52 |
| 56 | Discharge hose, through which a breathing gas sample is fed again into the ventilation circuit 40, leads to a feed point upstream of the carbon dioxide absorber 25a |
| 57 | Pressure sensor of the gas sensor array 50, measures the pressure $P_{cell}$ |
| 58 | Sensor for the ambient pressure $P_{amb}$ |
| 100 | Ventilator, configured as an anesthesia apparatus, comprises the optional anesthetic vaporizer 31, the delivery unit 24a, the carbon dioxide absorber 25a, the overpressure valve 29, the pressure sensor 36, the nonreturn valves 23a and 23b, the PEEP valve 24b and the manual ventilation bag 26 |
| 110 | Measuring system, comprises the gas sensor array 50, the water trap 51 and the signal processing unit 30 |
| Cov[CO2, O2] | Covariance between the time curves of the CO2 concentration and of the O2 concentration |
| DiPhaC | "Differential in Phase Covariance," first leak criterion based on time periods with the same sign |
| DPC | "Delta Pressure Covariance," second leak criterion based on the changes in covariance and pressure |
| L | Exemplary leak in the transition between the removal hose 52 and the water trap 51 |
| $P_{aw}$ | Breathing and ventilation pressure present at the patient 20, measured by the sensor 36 |
| $P_{amb}$ | Ambient pressure, measured by the sensor 58 |
| $P_{cell}$ | Pressure at the inlet of the gas sensor array 50, preferably the pressure in relation to the ambient pressure $P_{amb}$ |
| $P_{cell, abs}$ | Absolute pressure at the inlet of the gas sensor array 50, measured by the sensor 57 |
| $P_{limit}$ | Lower limit for the check whether a leak has actually occurred |
| T_L, T_L.1, T_L.2 | Time period, in which a leak L has occurred between the branching-off point 34 and the gas sensor array 50 |

What is claimed is:

1. A process for monitoring a measuring system for mechanical ventilation of a patient, the process comprising the steps of:

providing the measuring system, wherein the measuring system comprises: a gas sensor array and a gas sensor fluid-guiding unit, and wherein the process is performed while a fluid connection, between the patient and a medical device, is established, using a patient-side fluid-guiding unit;

with the measuring system, measuring a concentration of a gas flowing in the fluid connection between the patient and the medical device;

providing a signal processing unit and a control device;

automatically controlling a parameter of the mechanical ventilation, via the control device, as a function of the concentration of the gas;

suctioning a gas sample from the patient-side fluid-guiding unit and guiding the gas sample through the gas sensor fluid-guiding unit to the gas sensor array, with the fluid connection, between the patient and the medical device, being established;

with the signal processing unit, calculating an indicator of a progress over time of a concentration of carbon dioxide, as a carbon dioxide concentration time curve, in the suctioned gas sample and an indicator of a progress over time of a concentration of an other gas, different from carbon dioxide, as an other gas concentration time curve, in the suctioned gas sample, using measured values of the gas sensor array;

with the signal processing unit, calculating an indicator of a progress over time of a temporal change of the carbon dioxide concentration, as a carbon dioxide concentration change curve, and an indicator of a progress over time of a temporal change of the concentration of the other gas, as an other concentration change curve, using the carbon dioxide concentration time curve and the other gas concentration time curve;

with the signal processing unit, searching for time periods with a same sign, wherein throughout the same sign time period the two concentration change curves have the same sign, with both concentration change curves being greater than zero or both less than zero;

with the signal processing unit, checking, upon at least one same sign time period being detected, whether the two concentration change curves meet a predefined first leak criterion in the detected same sign time period;

with the signal processing unit, determining that a leak has occurred, the leak occurring between the patient-side fluid-guiding unit and the gas sensor array, or determining that there is an indication of such a leak, if the predefined first leak criterion is met; and if the signal processing unit has determined that the leak or leak indication has occurred, with the control device, generating an alarm and transmitting the alarm to a receiver located at a distance in space and outputting the alarm, wherein the alarm is configured to be perceptible to a person, and while the patient is mechanically ventilated, the mechanical ventilation is continued without using the results of the gas measurement of the concentration of the gas flowing in the fluid connection between the patient and the medical device.

2. The process in accordance with claim 1, wherein the predefined first leak criterion depends on at least one of the following parameters:

a duration of the same sign time period;

an entire duration of all same sign time periods detected since a predefined reference time;

an arithmetic product of the two values that the two concentration change curves assume at least one sample time in the same sign time period;

an arithmetic sum of a plurality of such arithmetic products of values with the same sign within the same sign time period; and a sum of all such arithmetic products for all sample times within at least one same sign time period.

3. The process in accordance with claim 1, wherein a calculation of a phase shift of the carbon dioxide concentration change curve in relation to the other concentration change curve is carried out such that, after the calculated phase shift, a maximum of the carbon dioxide concentration change curve falls at the same time point as a maximum or minimum of the other concentration change curve.

4. The process in accordance with claim 1, further comprising the steps of:

measuring a progress over time, as a pressure change curve, of a pressure at a measuring point in or at the gas sensor array or in or at the gas sensor fluid-guiding unit; and calculating an indicator of a progress over time of a temporal change of the measured pressure;

calculating an indicator of a phase shift between the carbon dioxide concentration time curve and the other gas concentration time curve;

calculating an indicator of a progress over time of a temporal change of the calculated phase shift indicator; and checking whether a predefined second leak criterion is met, wherein:

the predefined second leak criterion depends on the phase shift change curve and the pressure change curve;

upon detecting that at least one of the predefined first and second leak criteria is met, determining that the leak has occurred between the patient-side fluid-guiding unit and the gas sensor array or determining that there is the indication of the leak.

5. The process in accordance with claim 4, wherein the predefined second leak criterion depends on:

the phase shift change curve at a first sample time and the pressure change curve at a second sample time, wherein the time interval between the two sample times depends on the distance between the measuring point, at which the pressure is measured, and a measuring point, at which the two concentrations are measured.

6. The process in accordance with claim 5, wherein the predefined second leak criterion is met if:

the phase shift curve at the first sample time is above a first predefined threshold; and the pressure change curve at the second sample time is above a second predefined threshold.

7. The process in accordance with claim 1, wherein: upon detecting that at least one of the predefined first leak criterion and the predefined second leak criterion is met, carrying out a check;

the check comprises:

interrupting the step of suctioning the gas sample from the patient-side fluid-guiding unit;

measuring a pressure in the patient-side fluid-guiding unit and measuring a pressure at a measuring point in or at the measuring system while the suctioning of the gas sample is interrupted;

comparing the two measured pressures; and upon the result that the comparison of the two pressures meets a predefined third leak criterion, determining that a leak has occurred.

8. A measuring system for a mechanical ventilation of a patient, the measuring system comprising:

a gas sensor array;

a gas sensor fluid-guiding unit connected or connectable to a patient-side fluid-guiding unit, wherein, using the patient-side fluid-guiding unit, a fluid connection is established or establishable, the fluid connection configured to be between the patient and a medical device, wherein the patient is mechanically ventilated while a process for monitoring the measuring system is performed, wherein the measuring system is configured to suction gas from the patient-side fluid-guiding unit through the gas sensor fluid-guiding unit to the gas sensor array, wherein the gas sensor array is configured to measure a concentration of a gas flowing in the fluid connection between the patient and the medical device;

a control device, wherein the control device is configured to automatically control a parameter of the mechanical ventilation as a function of the concentration of the gas; and a signal processing unit configured to:

calculate an indicator of progress over time of a concentration of carbon dioxide, as a carbon dioxide concentration time curve, in the suctioned gas sample using measured values of the gas sensor array;

calculate an indicator of progress over time of a concentration of an other gas, different from carbon dioxide, as an other gas concentration time curve, in the suctioned gas sample using measured values of the gas sensor array;

calculate an indicator of a progress over time of a temporal change of the carbon dioxide concentration, as a carbon dioxide concentration change curve, using the carbon dioxide concentration time curve;

calculate an indicator of a progress over time of a temporal change of the concentration of the other gas, as an other gas concentration change curve, using the other gas concentration time curve;

search for time periods with a same sign, wherein throughout the same sign time period the two concentration change curves have the same sign, with both concentration change curves being greater than zero or both less than zero;

upon detecting at least one same sign time period, check whether the two concentration change curves meet a predefined first leak criterion in the detected at least one same sign time period;

upon the predefined first leak criterion being met, determining that a leak has occurred between the patient-side fluid-guiding unit and the gas sensor array or determining that there is an indication of such a leak, wherein the control device is configured to generate an alarm if the signal processing unit determines that the leak has occurred or that there is the indication of the leak and to transmit the alarm to a receiver and to provide the alarm as output such that the alarm is configured to be perceptible to a person, and wherein the mechanical ventilation is configured to be continued without using the results of the gas measurement of the concentration of the gas flowing in the fluid connection between the patient and the medical device if the signal processing unit determines that the leak has occurred or that there is the indication of the leak.

9. A connection device for mechanical ventilation of a patient, the connection device comprising:

a patient-side fluid-guiding unit; and a measuring system comprising:

a gas sensor array;

a gas sensor fluid-guiding unit connected or connectable to the patient-side fluid-guiding unit, wherein, using the patient-side fluid-guiding unit, a fluid connection is established or establishable, the fluid connection configured to be between the patient and a medical device, and whereby the patient is mechanically ventilated while a process for monitoring the measuring system is performed, wherein the measuring system is configured to suction gas from the patient-side fluid-guiding unit through the gas sensor fluid-guiding unit to the gas sensor array, the gas sensor array being configured to measure a concentration of a gas flowing in the fluid connection between the patient and the medical device;

a control device, wherein the control device is configured to automatically control a parameter of the mechanical ventilation as a function of the concentration of the gas;

and a signal processing unit configured to:

calculate an indicator of progress over time of a concentration of carbon dioxide with respect to time, as a carbon dioxide concentration time curve, in the suctioned gas sample using measured values of the gas sensor array;

calculate an indicator of progress over time of a concentration of an other gas, different from carbon dioxide, as an other gas concentration time curve, in the suctioned gas sample using measured values of the gas sensor array;

calculate an indicator of a progress over time of a temporal change of the carbon dioxide concentration, as a carbon dioxide concentration change curve, using the carbon dioxide concentration time curve;

calculate an indicator of a progress over time of a temporal change of the concentration of the other gas, as an other gas concentration change curve, using the other gas concentration time curve;

search for time periods with a same sign, wherein throughout the same sign time period the two concentration change curves have the same sign, with both concentration change curves being greater than zero or both less than zero;

upon detecting at least one same sign time period, check whether the two concentration change curves meet a predefined first leak criterion in the detected at least one same sign time period; and upon the predefined first leak criterion being met, determine that a leak has occurred between the patient-side fluid-guiding unit and the gas sensor array or determine that there is an indication of such a leak;

wherein the control device is further configured to generate an alarm if the signal processing unit determines that the leak has occurred or that there is the indication of the leak and to transmit the alarm to a receiver and to provide the alarm as output such that the alarm is configured to be perceptible to a person;

and wherein the mechanical ventilation is continuable or continued without using the results of the gas measurement of the concentration of a gas flowing in the fluid connection between the patient and the medical device if the signal processing unit determines that the leak has occurred or that there is the indication of the leak.

10. A medical system comprising: a medical device;

and a connection device comprising:

a patient-side fluid-guiding unit; and a measuring system comprising:

a gas sensor array;

a gas sensor fluid-guiding unit connected to or connectable to the patient-side fluid-guiding unit, wherein, using the patient-side fluid-guiding unit, a fluid connection is establishable, the fluid connection configured to be between the patient and the medical device, and whereby the patient is mechanically ventilated while a process for monitoring the measuring system is performed, wherein the measuring system is configured to suction gas from the patient-side fluid-guiding unit through the gas sensor fluid-guiding unit to the gas sensor array, wherein the measuring system is configured to measure a concentration of a gas flowing in the fluid connection between the patient and the medical device;

and a signal processing unit configured to:

calculate an indicator of a progress over time of a concentration of carbon dioxide, as a carbon dioxide concentration time curve, in the suctioned gas sample using measured values of the gas sensor array;

calculate an indicator of a progress over time of a concentration of an other gas, different from carbon dioxide, as an other gas concentration time curve, in the suctioned gas sample using measured values of the gas sensor array;

calculate an indicator of a progress over time of a temporal change of the carbon dioxide concentration, as a carbon dioxide concentration change curve, using the carbon dioxide concentration time curve;

calculate an indicator of a change over time of a temporal change of the concentration of the other gas, as an other concentration change curve, using the other gas concentration time curve;

search for time periods with a same sign, wherein during the same sign time period the two concentration change curves have the same sign throughout the same sign time period, with both concentration change curves being greater than zero or both less than zero;

upon detecting at least one same sign time period, check whether the two concentration change curves meet a predefined first leak criterion in the detected at least one same sign time period; and upon the predefined first leak criterion being met, determine that a leak has occurred between the patient-side fluid-guiding unit and the gas sensor array or determine that there is an indication of such a leak, wherein the medical device is configured:

to receive from the measuring system of the connection device measured time curves of the carbon dioxide concentration and of the concentration of the other gas; and at least one of: to process the received time curves, and to output the received time curves in a form configured to be perceptible by a person; a control device, wherein the control device is configured to automatically control a parameter of the mechanical ventilation as a function of the concentration of the gas;

wherein the control device is further configured to generate an alarm if the signal processing unit determines that the leak has occurred or that there is the indication of the leak and to transmit the alarm to a receiver and to provide the alarm as output such that the alarm is configured to be perceptible to a person; and wherein the mechanical ventilation is continued without using the results of the gas measurement of the concentration of the gas flowing in the fluid connection between the patient and the medical device if the signal processing unit determines that the leak has occurred or that there is the indication of the leak.

* * * * *